(12) United States Patent
Narumi et al.

(10) Patent No.: US 6,893,698 B2
(45) Date of Patent: May 17, 2005

(54) OPTICAL INFORMATION RECORDING MEDIUM, OPTICAL MEASURING METHOD AND OPTICAL INFORMATION RECORDING/REPRODUCING METHOD

(75) Inventors: Kenji Narumi, Ibaraki (JP); Kenichi Nishiuchi, Hirakata (JP); Naoyasu Miyagawa, Kawanishi (JP); Rie Kojima, Kadoma (JP); Takashi Nishihara, Hirakata (JP); Noboru Yamada, Hirakata (JP)

(73) Assignee: Matsushita Electric Industrial Co., Ltd., Osaka (JP)

(*) Notice: Subject to any disclaimer, the term of this patent is extended or adjusted under 35 U.S.C. 154(b) by 103 days.

(21) Appl. No.: 10/270,820

(22) Filed: Oct. 15, 2002

(65) Prior Publication Data

US 2003/0134077 A1 Jul. 17, 2003

(30) Foreign Application Priority Data

Oct. 12, 2001 (JP) .................................. 2001-314827
Mar. 12, 2002 (JP) .................................. 2002-067695

(51) Int. Cl.$^7$ ............................................. B32B 3/02
(52) U.S. Cl. ................... 428/64.1; 428/64.5; 428/64.6; 430/270.13
(58) Field of Search .................... 428/64.1, 64.4, 428/64.5, 64.6, 913; 430/270.13, 495.1, 945

(56) References Cited

U.S. PATENT DOCUMENTS

| 6,190,750 B1 | 2/2001 | Wierenga et al. |
| 6,221,455 B1 * | 4/2001 | Yasuda et al. ............. 428/64.1 |
| 6,456,584 B1 * | 9/2002 | Nagata et al. ........... 369/275.2 |

| 2002/0024913 A1 * | 2/2002 | Kojima et al. ................ 369/94 |
| 2002/0054983 A1 * | 5/2002 | Nishihara .................... 428/212 |

FOREIGN PATENT DOCUMENTS

| EP | EP 1 028 421 | 8/2000 |
| EP | EP 1 096 484 | 5/2001 |
| EP | EP 1 229 528 | 8/2002 |
| JP | 2001-209132 | 7/2001 |

OTHER PUBLICATIONS

European Search Report corresponding to application No. EP 02 02 2923 dated Jun. 26, 2003.
European Search Report corresponding to application No. EP 02 02 2923 dated May 22, 2003.
European Search Report for EP 02 02 2923, dated Feb. 27, 2003.

* cited by examiner

*Primary Examiner*—Elizabeth Mulvaney
(74) *Attorney, Agent, or Firm*—RatnerPrestia

(57) ABSTRACT

An optical information recording medium having two or more information layers, wherein the irradiation of either the information layer with a laser beam converging thereon causes information signals to be recorded or reproduced; the nearer positioned information layer than the farthest information layer as viewed from the incidence side of the laser beam has a recording layer varying between two optically detectable states, and $$0 \leq |T_c - T_a|/T_c \leq 0.1$$

where $T_c$ is the transmittance of the nearer positioned information layer when the recording layer is in state (a) and $T_a$, the transmittance, when it is in state (b). This makes possible accurate accurately recording and reproduction of information onto and out of the farther information layer irrespective of whether or not any information is recorded on the nearer information layer.

26 Claims, 11 Drawing Sheets

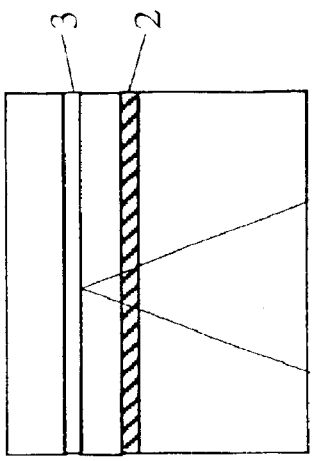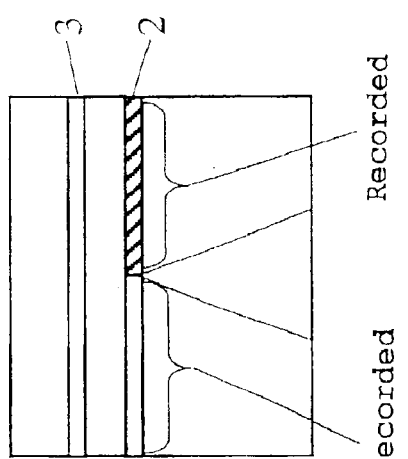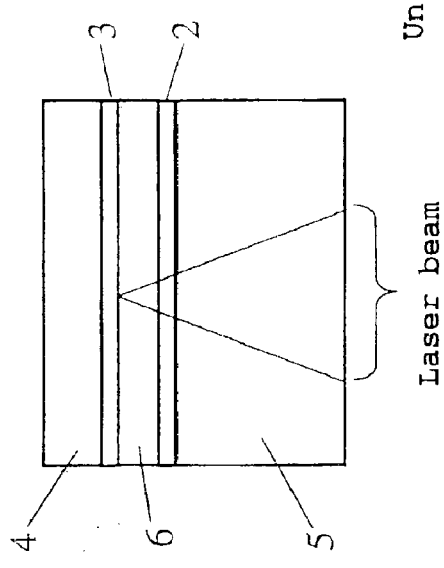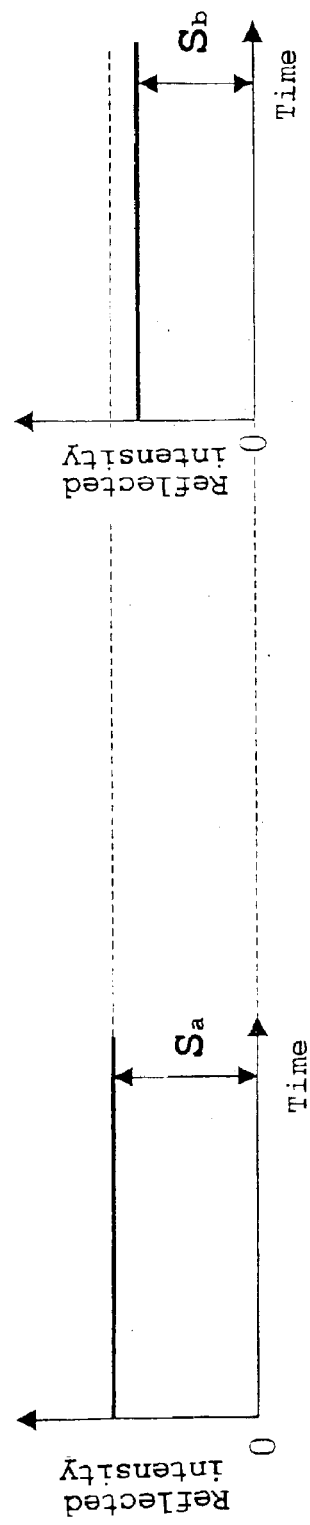

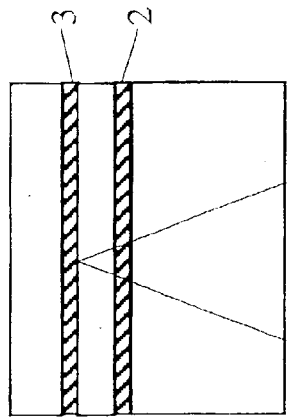
Fig. 10(a)
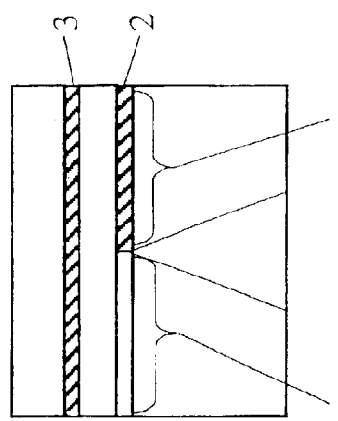
Fig. 10(b)
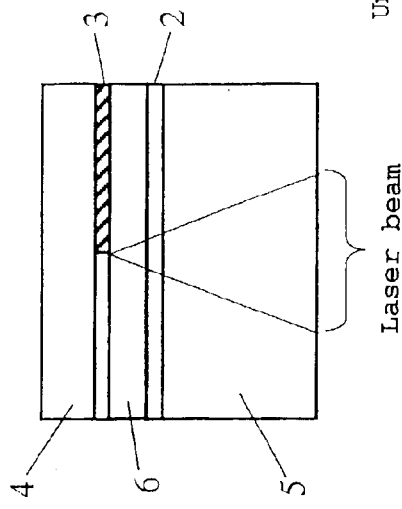
Fig. 10(c)
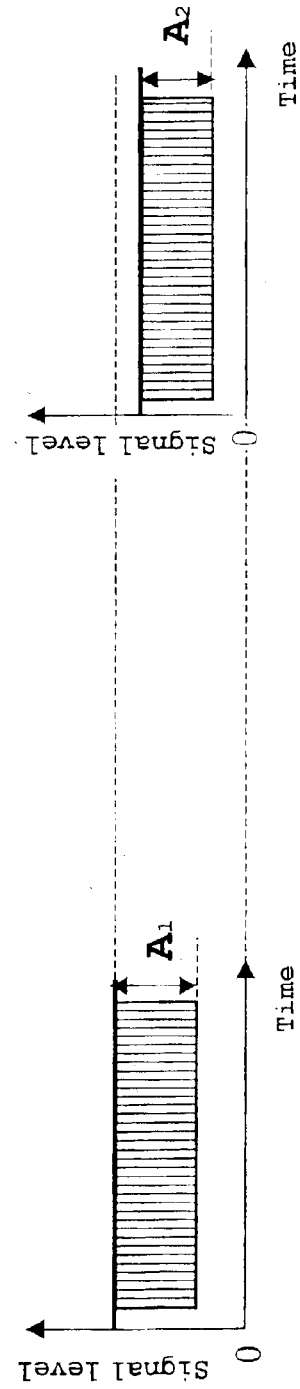

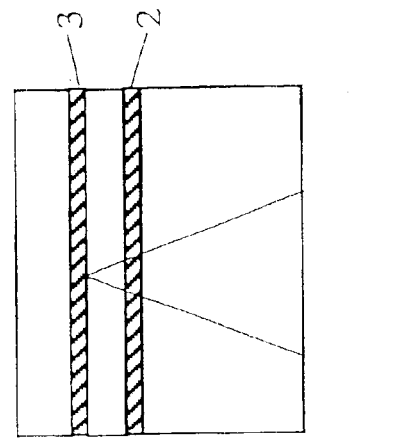
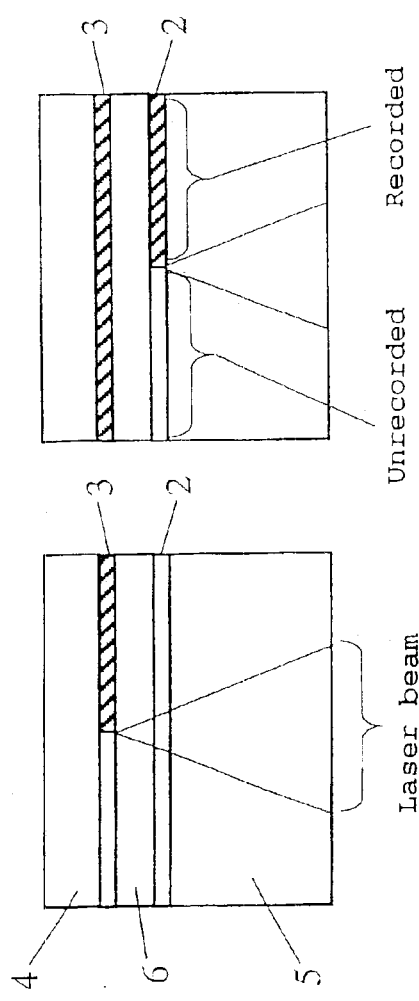
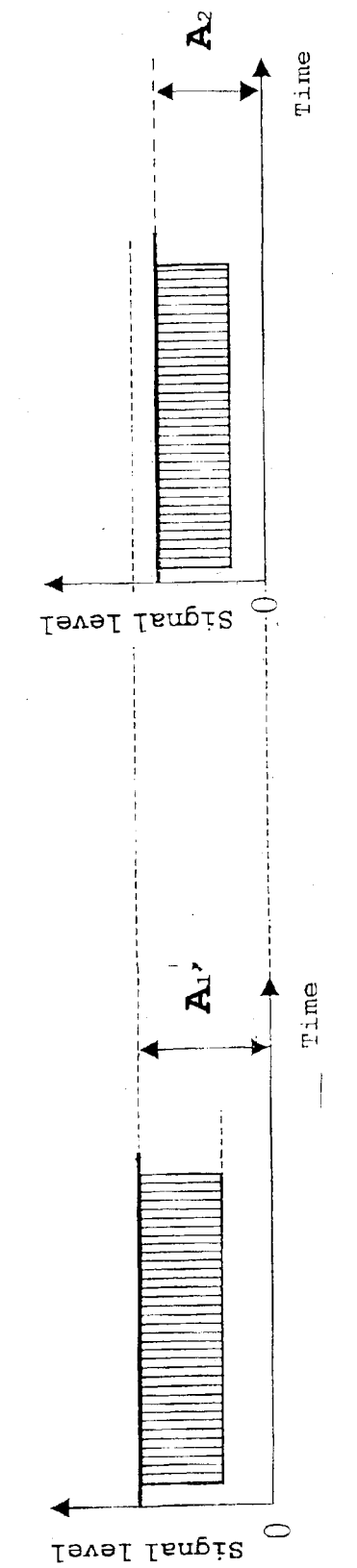

OPTICAL INFORMATION RECORDING MEDIUM, OPTICAL MEASURING METHOD AND OPTICAL INFORMATION RECORDING/REPRODUCING METHOD

BACKGROUND OF THE INVENTION

1. Field of the Invention

The present invention relates to an optical information recording medium and the like, such as an optical disk.

2. Related Art of the Invention

In recent years, optical disks, optical cards and optical tapes have been proposed and developed as media for optically recording information. Above all, optical disks are attracting note as media capable of recording and reproducing information in large capacity and in high density.

One of the erasable optical disk types is a phase change type optical disk. The recording film for use in the phase change type optical disk takes on either an amorphous state or a crystalline state depending on the conditions of heating or cooling with a laser beam, and the two states are reversible between each other. The optical constant of the recording film is different between the amorphous state and the crystalline state. In the phase change type optical disk, one or the other or the two states is selectively formed in the recording film according to information signals, and the resultant optical change (i.e. the change in transmittance or reflectivity) is utilized for recording or reproducing the information signals. In order to achieve the two states, the information signals are recorded by the following method.

When the recording film of the optical disk is irradiated in a pulse form with power for raising the temperature of the recording film above its melting point (hereinafter referred as peak power), the molten portion is quickly cooled with the passage of the laser beam to present a record mark of the amorphous state. Or when the recording film is irradiated with a converted laser beam of an intensity to raise the temperature of the recording film above its crystallization temperature but not over the melting point (hereinafter referred as bias power), the irradiated portion of the recording film turns into the crystalline state.

In addition, a keen requirement has emerged in recent years for higher density of optical disks. In connection with that, there has been proposed a multi-layered recording medium having two or more layers in the thickness direction of the disk wherein information can be recorded onto or reproduced out of each information layer.

However, when recording is to be done onto an information layer farther inside from the laser incidence side by the conventional method, there is a fear that the farther inside information layer is affected by the nearer information layer.

For instance, depending on whether or not any signal is recorded in a recording/reproducing area of an information recording layer, the transmittance of that layer differs. Accordingly there is a problem that, when recording is to be done on a farther information layer, the intensity of the laser beam reaching the farther information layer varies with the ratio between the amorphous area and the crystalline area in the laser spot on the nearer information recording layer, making it impossible to perform accurate recording.

A further problem is that, when data on the farther information layer are to be reproduced, the change in the transmittance depending on the recording state of the nearer information layer invites deterioration in the quality of reproduced signals.

SUMMARY OF THE INVENTION

The present invention is intended to solve these problems by providing an optical information recording medium and the like permitting accurate recording and reproduction of data onto and out of an information layer farther inside in a multi-layered recording medium.

One aspect of the present invention is an optical information recording medium having two information layers, converged irradiation of a laser beam onto any of said information layers causing information signals to be recorded or reproduced, wherein:

an information layer positioned nearer than the farthest information layer from the incidence side of said laser beam have a recording layer varying between two optically detectable states, the optical information recording medium having a configuration of:

$$0 \leq |T_c - T_a|/T_c \leq 0.1$$

where $T_c$ is the transmittance of said nearer positioned information layer when said recording layer is in state (a) and $T_a$ is the transmittance of the same when said recording layer is in state (b).

Another aspect of the present invention is an optical information recording medium having three or more information layers, converged irradiation of any of which with a laser beam causes information signals to be recorded or reproduced, characterized in that:

each of a plurality of information layers positioned nearer than the farthest information layer from the incidence side of said laser beam has a recording layer varying between two optically detectable states, the optical information recording medium having a configuration of:

$$0 \leq |T_c - T_{min}|/T_c \leq 0.1 \text{ and } 0 \leq |T_c - T_{max}|/T_c \leq 0.1$$

where $T_c$ is a synthesized transmittance of said plurality of information layers when every one of the respective recording layers of said plurality of information layer in state (a);

$T_{min}$ is a minimum value of the synthesized transmittances which are derived from combinations of said various states of the respective recording layers, and $T_{max}$ is a maximum value of the synthesized transmittances which are derived from combinations of said various states of the respective recording layers.

Still another aspect of the present invention is the optical information recording medium, further having a configuration of:

$$(T_a + T_c)/2 \geq 0.4$$

Yet still another aspect of the present invention is the optical information recording medium, as set forth in either first or third present invention, having a configuration of:

$$A_c < A_a \text{ and } R_c > R_a, \text{ or}$$

$$A_c > A_a \text{ and } R_c < R_a$$

where $A_c[\%]$ is the absorption index of said recording layer of an information layer positioned nearer than the farthest information layer from the incidence side of said laser beam when said recording layer is in state (a), and $A_a[\%]$ is the absorption index of the same when said recording layer is in state (b), and $R_c[\%]$ is the reflectivity of said nearer information layer when said recording layer is in state (a), and $R_a[\%]$ is the reflectivity of the same when it is in state (b).

Still yet another aspect of the present invention is the optical information recording medium, wherein:

an information layer positioned nearer than the farthest information layer from the incidence side of said laser beam has at least a first dielectric layer, a phase-change recording layer, a second dielectric layer and a metallic reflecting layer, and said layers are arranged in the order, from the incidence side inward, of said first dielectric layer, said phase-change recording layer, said second dielectric layer and said metallic reflecting layer.

A further aspect of the present invention is the optical information recording medium, wherein:

the wavelength of said laser beam is in the range of 390 nm to 430 nm, and said metallic reflecting layer consists of Ag or an alloy having Ag as its main constituent, having a configuration of:

$t_a \leq 12$ when $t_b \leq 18$, $t_a \leq 10$ when $18 < t_b \leq 22$, and $t_a \leq 32 - t_b$ when $22 < t_b < 30$ where $t_a$[nm] is the thickness of said phase-change recording layer, and $t_b$[nm] is that of said metallic reflecting layer.

A still further aspect of the present invention is the optical information recording medium, wherein:

an information layer positioned nearer than the farthest information layer from the incidence side of said laser beam has at least a first dielectric layer, a phase-change recording layer, a second dielectric layer, a metallic reflecting layer and a third dielectric layer, and said layers are arranged in the order, from the incidence side inward, of said first dielectric layer, said phase-change recording layer, said second dielectric layer, said metallic reflecting layer and said third dielectric layer.

A yet further aspect of the present invention is the optical information recording medium, wherein:

the wavelength of said laser beam is in the range of 390 nm to 430 nm, and said metallic reflecting layer consists of at least Ag or an alloy having Ag as its main constituent, having a configuration of:

$t_a \leq 12$ when $t_b \leq 18$, $t_a \leq 38 - t_b$ when $16 < t_b \leq 18$, $t_a \leq 10$ when $18 < t_b \leq 20$, $t_a \leq 30 - t_b$ when $20 < t_b \leq 24$ and $t_a \leq 28 - t_b$ when $24 < t_b \leq 26$ where $t_a$[nm] is the thickness of said phase-change recording layer, and $t_b$[nm] is that of said metallic reflecting layer.

A still yet further aspect of the present invention is the optical information recording medium, having a configuration of:

$A_c < A_a$ and $R_c > R_a$, or $A_c > A_a$ and $R_c < R_a$ where $A_c$[%] is the absorption index of said phase-change recording layer when said recording layer of an information layer positioned nearer than the farthest information layer from the incidence side of said laser beam is crystalline, and $A_a$[%] is the absorption index of the same when said recording layer is amorphous, and $R_c$[%] is the reflectivity of said information layer when said recording layer is crystalline, and $R_a$[%] is the reflectivity of the same when it is amorphous.

And the first optical measuring method of the present invention is the following 10-th present invention for example.

An additional aspect of the present invention is an optical measuring method whereby a laser beam is converged on an optical information recording medium having two information layers, converged irradiation of the laser beam onto any of said information layers causing information signals to be recorded or reproduced, wherein an information layer positioned nearer than the farthest information layer from the incidence side of said laser beam has a recording layer varying between two optically detectable states, and said laser beam reflected by any of said information layers is received by a photodetector to measure changes in transmittance, comprising:

a step of measuring with said photodetector the intensity of said laser beam coming out of said optical information recording medium when the area transmitting said laser beam in the recording layer contained in said nearer positioned information layer is in state (a), the intensity being represented by $S_a$, wherein said laser beam has first been transmitted by said nearer positioned information layer, then been reflected by the farthest information layer, and again been transmitted by said nearer positioned information layer so that the laser beam comes out of said optical information recording medium, a step of measuring with said photodetector the intensity of said laser beam coming out of said optical information recording medium when the area transmitting said laser beam in the recording layer contained in said nearer positioned information layer is in state (b), the intensity being represented by $S_b$, wherein said laser beam has first been transmitted by said nearer positioned information layer, then been reflected by the farthest information layer, and again been transmitted by said nearer positioned information layer so that the laser beam comes out of said optical information recording medium, and a step of deriving a change in the transmittance of said nearer positioned information layer on the basis of said $S_a$ and $S_b$.

A still additional aspect of the present invention is an optical measuring method whereby a laser beam is converged on an optical information recording medium having three or more information layers, converged irradiation of the laser beam onto any of said information layers causing information signals to be recorded or reproduced, wherein a plurality of information layers positioned nearer than the farthest information layer from the incidence side of said laser beam have a recording layer varying between two optically detectable states, and said laser beam reflected by any of said information layers is received by a photodetector to measure changes in transmittance, case (a) is such case that a synthesized transmittance of said plurality of information layers is minimum value within the synthesized transmittances which are derived from combinations of said various states of the respective recording layers, and case (b) is such case that a synthesized transmittance of said plurality of information layers is maximum value within the synthesized transmittances which are derived from combinations of said various states of the respective recording layers, and comprising:

a step of measuring with said photodetector the intensity of said laser beam coming out of said optical information recording medium when the combination of the states of the recording layers of said nearer plurality of the information layers is in the case (a), the intensity being represented by $S_a$, wherein said laser beam has first been transmitted by said nearer plurality of the information layers, then been reflected by a predetermined information layer located farther inside than the information layer that has transmitted the beam, and again been transmitted by said nearer plurality of the information layers so that the laser beam comes out of said optical information recording medium, a step of measuring with said photodetector the intensity of said laser beam coming out of said optical information recording medium when the combination of the states of the recording layers of said nearer plurality of the information layers is in the case (b), the intensity being represented by $S_b$, wherein said laser beam has first been transmitted by said nearer plurality of the information layers, then been reflected by the farthest information layer, and again been transmitted by said nearer plurality of the information layers so that the laser beam comes out of said optical information recording medium, and a step of deriving a change in the transmittance of said nearer plurality of the information layers on the basis of said $S_a$ and $S_b$.

A yet additional aspect of the present invention is an optical measuring method whereby a laser beam is converged on an optical information recording medium having two information layers, converged irradiation of the laser beam onto any of said information layers causing information signals to be recorded or reproduced, wherein an information layer positioned nearer than the farthest information layer from the incidence side of said laser beam has a recording layer varying between two optically detectable states, and said laser beam reflected by any of said information layers is received by a photodetector to measure changes in strength of the laser beam, comprising:

a step of measuring with said photodetector the intensity of said laser beam coming out of said optical information recording medium when the area transmitting said laser beam in the recording layer contained in said nearer positioned information layer is in state (a), the intensity being represented by $S_a$, wherein said laser beam has first been transmitted by said nearer positioned information layer, then been reflected by the farthest information layer, and again been transmitted by said nearer positioned information layer so that the laser beam comes out of said optical information recording medium, a step of measuring with said photodetector the intensity of said laser beam coming out of said optical information recording medium when the area transmitting said laser beam in the recording layer contained in said nearer positioned information layer is in state (b), the intensity being represented by $S_b$, wherein said laser beam has first been transmitted by said nearer positioned information layer, then been reflected by the farthest information layer, and again been transmitted by said nearer positioned information layer so that the laser beam comes out of said optical information recording medium, and a step of deriving a change in the strength of the laser beam on the basis of said $S_a$ and $S_b$.

A still yet additional aspect of the present invention is an optical measuring method whereby a laser beam is converged on an optical information recording medium having three or more information layers, converged irradiation of the laser beam onto any of said information layers causing information signals to be recorded or reproduced, wherein a plurality of information layers positioned nearer than the farthest information layer from the incidence side of said laser beam have a recording layer varying between two optically detectable states, and said laser beam reflected by any of said information layers is received by a photodetector to measure changes in the strength of the laser beam, case (a) is such case that a synthesized transmittance of said plurality of information layers is minimum value within the synthesized transmittances which are derived from combinations of said various states of the respective recording layers, and case (b) is such case that a synthesized transmittance of said plurality of information layers is maximum value within the synthesized transmittances which are derived from combinations of said various states of the respective recording layers, and comprising:

a step of measuring with said photodetector the intensity of said laser beam coming out of said optical information recording medium when the combination of the states of the recording layers of said nearer plurality of the information layers is in the case (a), the intensity being represented by $S_a$, wherein said laser beam has first been transmitted by said nearer plurality of the information layers, then been reflected by a predetermined information layer located farther inside than the information layer that has transmitted the beam, and again been transmitted by said nearer plurality of the information layers so that the laser beam comes out of said optical information recording medium, a step of measuring with said photodetector the intensity of said laser beam coming out of said optical information recording medium when the combination of the states of the recording layers of said nearer plurality of the information layers is in the case (b), the intensity being represented by $S_b$, wherein said laser beam has first been transmitted by said nearer plurality of the information, layers, then been reflected by the farthest information layer, and again been transmitted by said nearer plurality of the information layers so that the laser beam comes out of said optical information recording medium, and a step of deriving a change in the strength of the laser beam on the basis of said $S_a$ and $S_b$.

By such measuring methods of the 12-th or 13-th present invention the amount of the change of the transmittance of the nearer positioned information layer can be easily obtained without measuring the transmission foctor.

And the second optical measuring method of the present invention is the following 14-th present invention for example.

A supplementary aspect of the present invention is an optical measuring method whereby a laser beam is converged on an optical information recording medium having two information layers, converged irradiation of the laser beam onto any of said information layers causing information signals to be recorded or reproduced, wherein an information layer positioned nearer than the farthest information layer from the incidence side of said laser beam has a recording layer varying between two optically detectable states, and said laser beam reflected by any of said information layers is received by a photodetector to measure changes in transmittance, comprising:

a step of measuring with said photodetector a modulation amplitude of said laser beam coming out of said optical information recording medium when the area transmitting said laser beam in the recording layer contained in said nearer positioned information layer is in state (a), the modulation amplitude being represented by $A_1$, wherein the laser beam has first been transmitted by said nearer positioned information layer, then been modulated by said information signals recorded on the farthest information layer, and again been transmitted by said nearer positioned information layer so that the laser beam comes out of said optical information recording medium, a step of measuring with said photodetector the modulation amplitude of said laser beam coming out of said optical information recording medium when a part of or the whole of the area transmitting said laser beam in the recording layer contained in said nearer positioned information layer is in state (b), the modulation amplitude being represented by $A_2$, wherein the laser beam has first been transmitted by said nearer positioned information layer, then been modulated by said information signals recorded on the farthest information layer, and again been transmitted by said nearer positioned information layer so that the laser beam comes out of said optical information recording medium, and a step of deriving a change in the transmittance of said nearer positioned information layer on the basis of said $A_1$ and $A_2$.

A still supplementary aspect of the present invention is an optical measuring method whereby a laser beam is converged on an optical information recording medium having three or more information layers, converged irradiation of the laser beam onto any of said information layers causing information signals to be recorded or reproduced, wherein a plurality of the information layers positioned nearer than the farthest information layer from the incidence side of said laser beam have a recording layers each varying between two optically detectable states, and said laser beam reflected by any of said information layers is received by a photodetector to changes in transmittance, and case (a) is such case that a synthesized transmittance of said plurality of information layers is minimum value within the synthesized transmittances which are derived from combinations of said various states of the respective recording layers, and case (b) is such case that a synthesized transmittance of said plurality of information layers is maximum value within the synthesized transmittances which are derived from combinations of said various states of the respective recording layers, and comprising:

a step of measuring with said photodetector a modulation amplitude of said laser beam coming out of said optical information recording medium when the combination of the states of the recording layers of said nearer plurality of the information layers is in the case (a), the modulation amplitude being represented by $A_1$, wherein the laser beam has first been transmitted by said nearer plurality of the information layers, then been modulated by said information signals recorded on a predetermined information layer located farther inside than the information layer that has transmitted the beam, and again been transmitted by said nearer plurality of the information layers so that the laser beam comes out of said optical information recording medium, a step of measuring with said photodetector a modulation amplitude of said laser beam coming out of said optical information recording medium when the combination of the states of the recording layers of said nearer plurality of the information layers is in the case (b), the modulation amplitude being represented by $A_2$, wherein the laser beam has first been transmitted by said nearer plurality of the information layers, then been modulated by said information signals recorded on the farthest information layer, and again been transmitted by said nearer plurality of the information layers so that the laser beam comes out of said optical information recording medium, and a step of deriving a change in the transmittance of said nearer positioned information layer on the basis of said $A_1$ and $A_2$.

A yet supplementary aspect of the present invention is an optical measuring method whereby a laser beam is converged on an optical information recording medium having two information layers, converged irradiation of the laser beam onto any of said information layers causing information signals to be recorded or reproduced, wherein an information layer positioned nearer than the farthest information layer from the incidence side of said laser beam has a recording layer varying between two optically detectable states, and said laser beam reflected by any of said information layers is received by a photodetector to measure changes in a modulation amplitude of the laser beam, comprising:

a step of measuring with said photodetector a modulation amplitude of said laser beam coming out of said optical information recording medium when the area transmitting said laser beam in the recording layer contained in said nearer positioned information layer is in state (a), the modulation amplitude being represented by $A_1$, wherein the laser beam has first been transmitted by said nearer positioned information layer, then been modulated by said information signals recorded on the farthest information layer, and again been transmitted by said nearer positioned information layer so that the laser beam comes out of said optical information recording medium, a step of measuring with said photodetector the modulation amplitude of said laser beam coming out of said optical information recording medium when a part of or the whole of the area transmitting said laser beam in the recording layer contained in said nearer positioned information layer is in state (b), the modulation amplitude being represented by $A_2$, wherein the laser beam has first been transmitted by said nearer positioned information layer, then been modulated by said information signals recorded on the farthest information layer, and again been transmitted by said nearer positioned information layer so that the laser beam comes out of said optical information recording medium, and a step of deriving a change in the modulation amplitude of the laser beam on the basis of said $A_1$ and $A_2$.

A still yet supplementary aspect of the present invention is an optical measuring method whereby a laser beam is converged on an optical information recording medium having three or more information layers, converged irradiation of the laser beam onto any of said information layers causing information signals to be recorded or reproduced, wherein a plurality of the information layers positioned nearer than the farthest information layer from the incidence side of said laser beam have a recording layers each varying between two optically detectable states, and said laser beam reflected by any of said information layers is received by a photodetector to measure changes in a modulation amplitude of the laser beam, and case (a) is such case that a synthesized transmittance of said plurality of information layers is minimum value within the synthesized transmittances which are derived from combinations of said various states of the respective recording layers, and case (b) is such case that a synthesized transmittance of said plurality of information layers is maximum value within the synthesized transmittances which are derived from combinations of said various states of the respective recording layers, and comprising:

a step of measuring with said photodetector a modulation amplitude of said laser beam coming out of said optical information recording medium when the combination of the states of the recording layers of said nearer plurality of the information layers is in the case (a), the modulation amplitude being represented by $A_1$, wherein the laser beam has first been transmitted by said nearer plurality of the information layers, then been modulated by said information signals recorded on a predetermined information layer located farther inside than the information layer that has transmitted the beam, and again been transmitted by said nearer plurality of the information layers so that the laser beam comes out of said optical information recording medium, a step of measuring with said photodetector a modulation amplitude of said laser beam coming out of said optical information recording medium when the combination of the states of the recording layers of said nearer plurality of the information layers is in the case (b), the modulation amplitude being represented by $A_2$, wherein the laser beam has first been transmitted by said nearer plurality of the information layers, then been modulated by said information signals recorded on the farthest information layer, and again been transmitted by said nearer plurality of the information layers so that the laser beam comes out of said optical information recording medium, and a step of deriving a change in the modulation amplitude of the laser beam on the basis of said $A_1$ and $A_2$.

By such measuring methods of the 16-th or 17-th present invention the amount of the change of the transmittance of the nearer positioned information layer can be easily obtained without measuring the transmission foctor.

Another aspect of the present invention is an optical measuring method, wherein the difference $A_{1'}$ between a zero level and upper envelope of the modulation amplitude is measured instead of the modulation amplitude $A_1$ of the laser beam, the difference $A_{2'}$ between a zero level and upper envelope of the modulation amplitude is measured instead of the modulation amplitude $A_2$ of the laser beam, and the change in the upper envelope of the modulation amplitude of the laser beam is detected on the basis of the $A_{1'}$ and $A_{2'}$ instead of that the change in the modulation amplitude of the laser beam is detected on the basis of the $A_1$ and $A_2$.

Still another aspect of the present invention is The optical measuring method, whereby, when the area in which said laser beam transmits of the recording layer contained in the nearer information layer is in state (b), after recording information signals on the farthest information layer, the modulation amplitude $A_2$ is measured.

Yet still another aspect of the present invention is the optical measuring method, wherein said state (a) is a crystalline state and said state (b) is an amorphous state.

Still yet another aspect of the present invention is the optical measuring method, wherein the recording layer of said nearer positioned information layer is, when said $S_b$ or $A_2$ or $A_{2'}$ is be measured, in a state consisting of many recording marks in an amorphous state and crystalline portions around them.

A further aspect of the present invention is The optical measuring method, said state (a) is an amorphous state and said state (b) is a crystalline state.

A still further aspect of the present invention is the optical measuring method, wherein the recording layer of said nearer positioned information layer is, when said $S_b$ or $A_2$ or $A_{2'}$ is be measured, in a state consisting of many recording marks in a crystalline state and amorphous portions around them.

A yet further aspect of the present invention is an optical information recording medium having a configuration of:

$$0 \leq |1+(S_b/S_a)^{1/2}| \leq 0.1\alpha$$

where $\alpha$ is the ratio of the area of said recording mark portion to the area where said laser beam is transmitted when said $S_b$ used in the optical measuring method described in the 10-th present invention is measured.

A still yet further aspect of the present invention is an optical information recording medium having a configuration of:

$$0 \leq |1-(A_2/A_1)^{1/2}| \leq 0.1\alpha$$

where $\alpha$ is the ratio of the area of said recording mark portion to the area where said laser beam is transmitted when said $A_2$ used in the optical measuring method described in the 14-th present invention is measured.

An additional aspect of the present invention is an optical information recording/reproducing method of recording or reproducing information signals by irradiating the optical information recording medium with a laser beam, whereby:

information signals are recorded or reproduced by irradiating one of two or more information layers with said laser beam from one side of said optical information recording medium.

BRIEF DESCRIPTION OF THE DRAWINGS

FIGS. 9(a)–9(c) are schematic diagrams illustrating the procedure of a first optical measuring method in the embodiment the invention.

FIGS. 10(a)–10(c) are schematic diagrams illustrating the procedure of a second optical measuring method in the embodiment the invention.

FIGS. 11(a)–11(c) are schematic diagrams illustrating the procedure of a third optical measuring method in the embodiment the invention;

DESCRIPTION OF SYMBOLS

Figure 1:
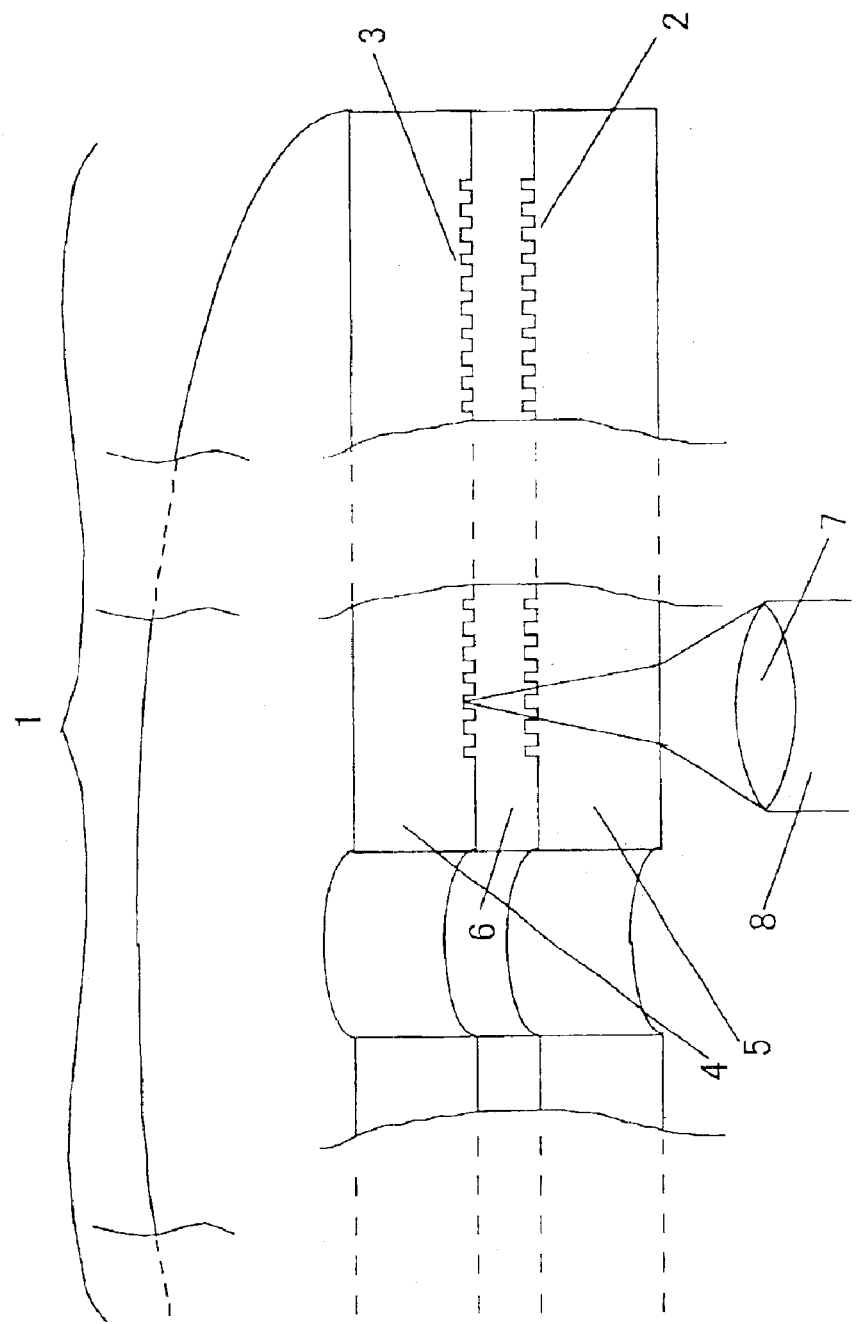
FIG. 1 is an external view and a section of an optical information recording medium in a first mode of implementing the present invention.

1 Optical disk
2 First information layer

3 Second information layer
4, 5 Substrates
6 Middle layer
7 Objective lens
8 Laser beam
9 First dielectric layer
10 Second dielectric layer
11 Recording layer
12 Reflecting layer
13 Third dielectric layer

PREFERRED EMBODIMENTS OF THE INVENTION

The present invention will be described in more specific terms below with reference to the following embodiments.

Figure 2:
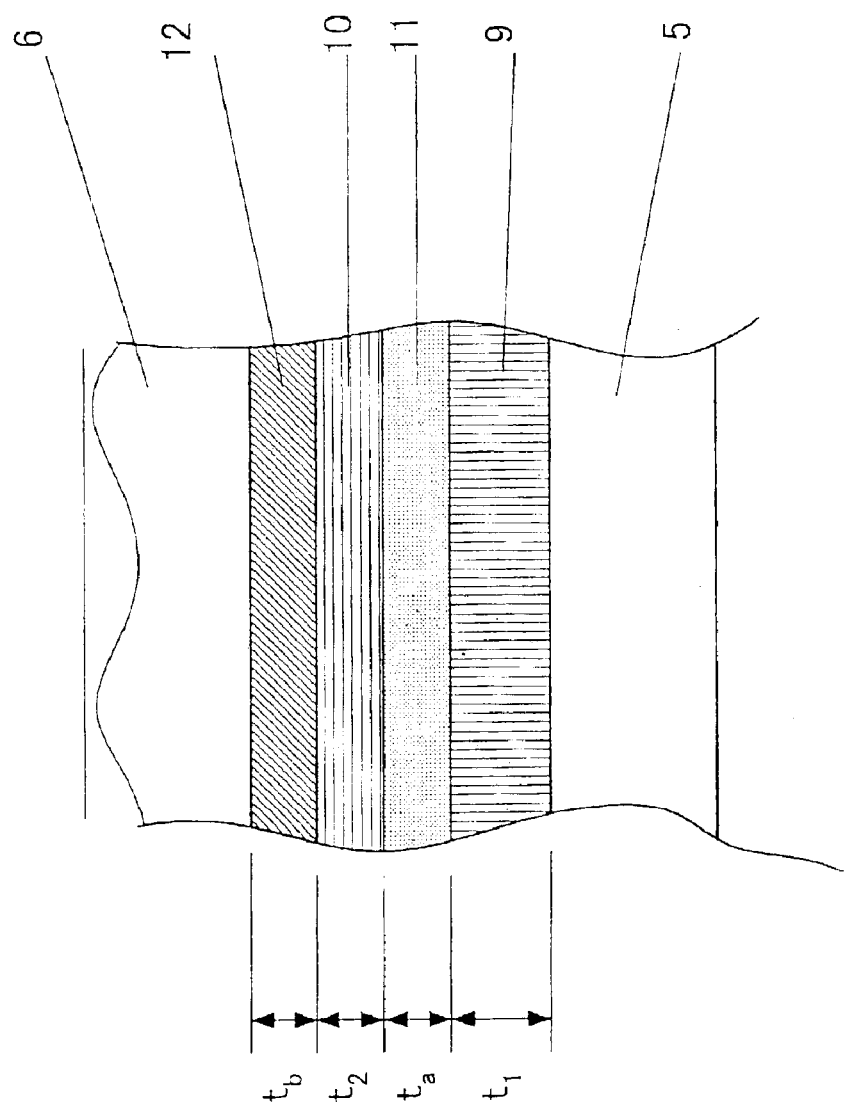
FIG. 2 is a section of a first information layer in the first embodiment.

FIG. 1 and FIG. 2 are schematic diagrams of an optical information recording medium in a first embodiment of implementing the invention.

A section of an optical disk 1 in FIG. 1 is shown in FIG. 2. FIG. 2 shows an optical disk having two information recording layers and a state in which it is irradiated with a laser beam. The optical disk 1 has a first information layer 2 positioned nearer to the light source and a second information layer 3 positioned farther from it. Each information layer is fabricated by forming a groove or a phase pit in a substrate 4 or 5 in advance and forming films of a dielectric layer, a recording layer, a reflecting layer and the like. The substrates are adhered with an ultraviolet ray-setting resin or the like to form an intermediate layer 6.

Alternatively, it is also acceptable to form, after forming each of the layers constituting the second information layer 3 in the substrate 4 in which a groove or a phase pit is already formed, the intermediate layer 6 having a groove or a phase pit and to combine, after forming each of the layers constituting the first information layer 2, the substrate 5 (also referred to as a cover layer).

Flat transparent plates of glass, resin or the like is used for the substrates 4 and 5. Alternatively, they may be formed by dissolving a resin in a solvent coating, and drying.

FIG. 2 is a sectional view showing an example of the configuration of the first information layer 2 constituting the nearer information layer in FIG. 1 as viewed from the incidence side of the laser beam.

For a first dielectric layer 9 and a second dielectric layer 10 over the substrate 5, oxides such as $SiO_2$, SiO, $TiO_2$, MgO or $GeO_2$, nitrides such as $Si_3N_4$, BN or AlN, sulfides such as ZnS or PbS or their mixtures can be used.

As a recording film material of a recording layer 11, a material undergoing a phase change between amorphous and crystalline states, for instance an SbTe-based, InTe-based, GeTeSn-based, SbSe-based, TeSeSb-based, SnTeSe-based, InSe-based, TeGeSnO-based, TeGeSnAu-based, TeGeSnSb-based, or TeGeSb-based chalcogen compound, can be used. A Te—$TeO_2$-based, Te—$TeO_2$—Au-based, Te—$TeO_2$—Pd-based or some other oxide-based material may also be used. Any of these materials gives rise to a phase change between a crystalline state (corresponding to state (a)) and an amorphous state (corresponding to state (b)). The material may as well be an AgZn-based or InSb-based metallic compound giving rise to a phase change between one crystalline state (state (a)) and another crystalline state (state (b)).

As a reflecting layer 12, a metallic material such as Au, Ag, Al or Cu or a dielectric multi-layered film having a high reflectivity at a predetermined wavelength can be used.

Films can be formed from these materials by vacuum vapor deposition or sputtering.

To add, the second information layer 3 may be in any form if it can detect optical changes of the reflected ray as information with a laser beam. Similarly to the first information layer 2, it may be a multi-layered film containing a phase-change recording layer or a multi-layered film containing a magneto-optical recording layer or a dye layer. Or it may be in a form of being recorded as a phase pit in the substrate 4.

A key point of the invention is that the transmittances of the first information layer 2 in two states before and after recording (recorded state and unrecorded (erased) state) are equalized by appropriately choosing the film thickness of each layer in the configuration described above, so that the intensity of the laser beam reaching the second information layer at the time of recording or re production can remain equal in any state. Further, the intensity of the laser beam reaching the second information layer should be sufficient for recording and reproduction. Incidentally, the following description will refer by way of example to a case in which the unrecorded (erased) part is in a crystalline state and the recorded part is in an amorphous state.

The transmittance of the first information layer 2 can be figured out by a calculation known as the matrix method from the optical constant and film thickness of the material of each layer constituting the first information layer (the matrix method is described in, for instance, Hiroshi Kubota, Hado Kogaku (Wave Optics), Iwanami Shoten, 1971, Chapter 3) which is incorporated herein by reference.

Table 1 shows an example of film thickness configuration of the first information layer 2 of a disk produced on a trial basis in this embodiment, its calculated transmittances in the amorphous state ($T_a$) and in the crystalline state ($T_c$), reflectivities in the amorphous state ($R_a$) and the crystalline state ($R_c$), absorption indices in the amorphous state ($A_a$) and the crystalline state ($A_c$), transmittance ratio between the amorphous state and the crystalline state ($T_c-T_a$)/$T_c$, and average transmittance ($T_a+T_c$)/2.

TABLE 1

| Disk | $t_a$ [nm] | $t_b$ [nm] | $t_1$ [nm] | $t_2$ [nm] | $R_c$ [%] | $R_a$ [%] | $T_c$ [%] | $T_a$ [%] | $A_c$ [%] | $A_a$ [%] | Transmittance ratio [%] | Average transmittance [%] |
|---|---|---|---|---|---|---|---|---|---|---|---|---|
| (1) | 6 | 6 | 45 | 12 | 6 | 0 | 48 | 47 | 42 | 49 | 2 | 47 |
| (2) | 10 | 12 | 40 | 45 | 3 | 9 | 46 | 41 | 42 | 41 | 10 | 44 |
| (3) | 8 | 20 | 40 | 68 | 25 | 18 | 40 | 41 | 18 | 23 | −5 | 41 |
| (4) | 14 | 10 | 22 | 40 | 15 | 23 | 32 | 28 | — | — | 13 | 30 |
| (5) | 14 | 30 | 68 | 12 | 34 | 9 | 5 | 7 | — | — | −41 | 6 |
| (6) | 12 | 26 | 62 | 50 | 19 | 31 | 29 | 23 | — | — | 21 | 26 |

In this embodiment, to equalize the intensities of the laser beam reaching the second information layer at the time of recording or reproduction between the amorphous state and the crystalline state, the smaller the absolute value of the transmittance ratio $(T_c-T_a)/T_c$, the more desirable. It is also desirable to maximize the average transmittance $(T_a+T_c)/2$ to secure a sufficient level of the intensity of the laser beam reaching the second information layer for recording and reproduction. In this embodiment, as shown in Table 1, six kinds of disks differing in transmittance ratio and average transmittance of the first information layer 2 were prepared by varying the thickness $t_a$ of the recording layer, the thickness $t_b$ of the reflecting layer, the thickness $t_1$ of the first dielectric layer and the thickness $t_2$ of the second dielectric layer.

Each disk was fabricated in the following manner. As the substrate 4, a polycarbonate plate of 120 mm in diameter and 1.1 mm in thickness was used, and a spiral groove of 0.25 µm in width, 0.32 µm in pitch and 20 nm in depth was formed in its surface. The second information layer 3 was formed over the surface of this substrate 4, and a reflecting layer of AgPdCu (0.32 to 2.06 i in optical constant) in a thickness of 100 nm, a dielectric layer of ZnS—SiO$_2$ (2.25 to 0.00 i in optical constant) in 15 nm, a recording layer of GeSbTe (1.78 to 3.51 i in the crystalline state and 3.31 to 2.29 i in the amorphous state in optical constant 3.31–2.29 i) in 12 nm and a dielectric layer of ZnS—SiO$_2$ in 60 nm were formed in succession.

Next, the recording layer of the second information layer 3 was varied from the amorphous state into the crystalline state to initialize it by irradiation with a laser beam, followed by the formation of the intermediate layer 6 to which the same groove shape as that in the substrate 4 was transcribed.

Further, as the first information layer 2, a reflecting layer of AgPdCu was formed in a thickness of $t_b$ nm, a second dielectric layer of ZnS—SiO$_2$ in $t_2$ nm, a recording layer of GeSbTe in $t_a$ nm and a first dielectric layer of ZnS—SiO$_2$ in $t_1$ nm in succession. After the formation of these films, the recording layer of the first information layer 2 was initialized by varying it from the amorphous state to the crystalline state by irradiation with a laser beam.

Finally, the substrate 5 consisting of polycarbonate was adhered with ultraviolet ray-setting resin. The total thickness of the adhesive portion and the substrate 5 was set to 0.1 mm.

A recording/reproducing test was carried out using these six different disks. Each disk was turned at a linear speed of 5 m/s, either one of the information layers 2 and 3 of the disk was irradiated with a semiconductor laser beam of 405 nm in wavelength, narrowed down with an objective lens of 0.85 in numerical aperture (NA).

As the modulation code for recording and reproduction, (8–16) modulation is used, and the modulated signals are turned into multi-pulse to generate the semiconductor laser. The mark length of 3T was set to be 0.20 µm.

Figure 3:
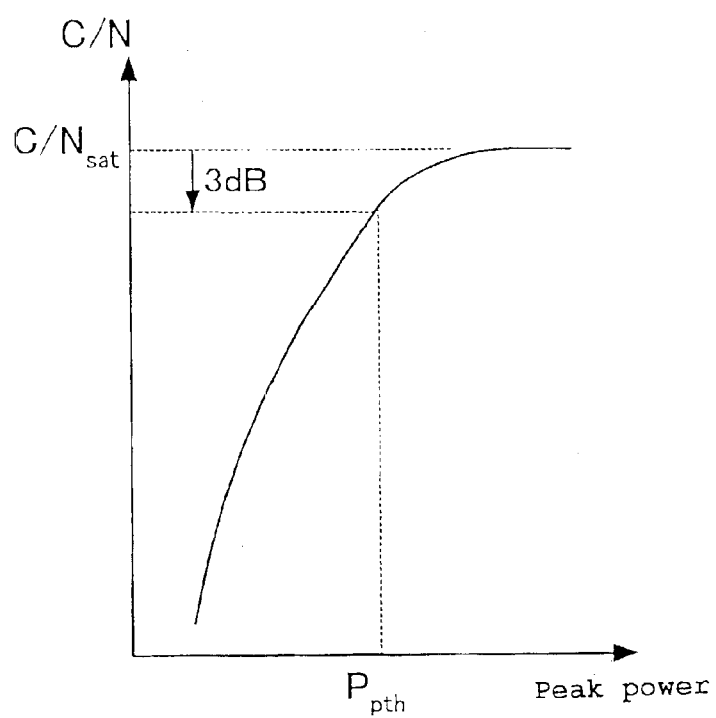
FIG. 3 is a diagram showing the peak power-dependence of C/N in the first embodiment.

Next will be described the method of setting the recording power with reference to FIG. 3. In a state in no recording is done on the first information layer 2, 3T periodic signals were recorded onto the second information layer 3 by varying the peak power, and the C/N of the reproduced signals was measured after the recording. The peak power-dependence of the C/N was plotted as shown in FIG. 3 and, with the peak power of (saturated C/N−3 dB) being represented by $P_{pth}$, the optimal peak power $P_{ps}$ used for information recording was calculated, which was defined to be:

$$P_{ps}=P_{pth}\times 1.2$$

The optimal bias power was figured out as the bias power Pbo which would give the highest erasion rate by varying the bias power with the peak power kept constant, recording 3T signals and later overwriting 11T signals.

Next will be described the influence of the first information layer, positioned nearer the light source, on the farther positioned second information layer.

Random signals were recorded in a half round area from the inner most circumference to the outermost circumference of the first information layer 2.

Figure 7:
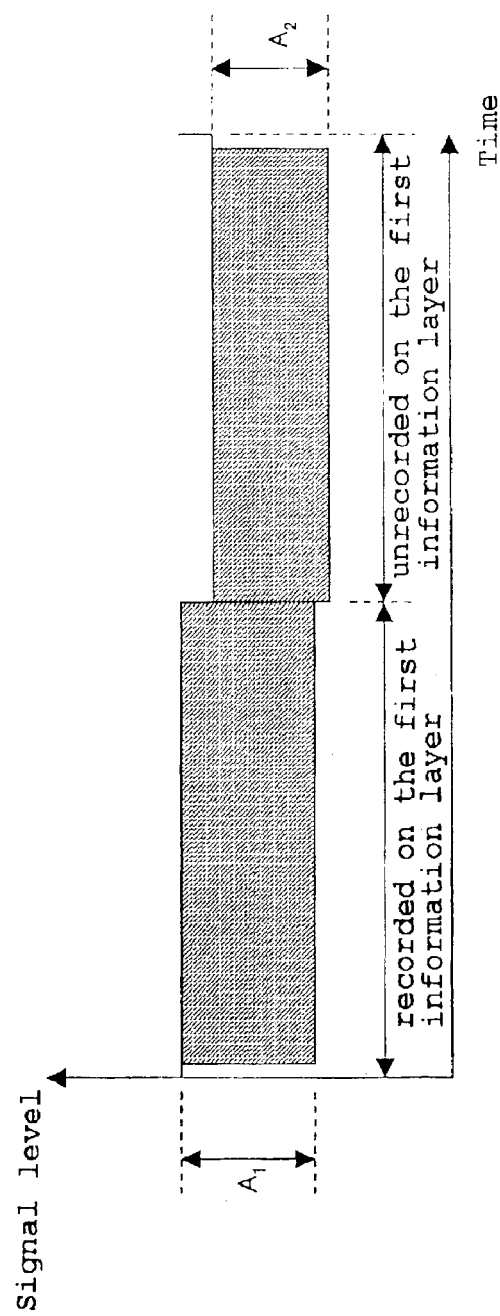
FIG. 7 is a diagram showing the waveform of a reproduced signal from the second information recording layer in the first and second modes of implementation.

Further, when 3T periodic signals were recorded for a full round of one track on the second information layer 3 with a peak power of $P_{ps}$ and a bias power of Pbo and these signals were reproduced, the amplitude of the reproduced signals fluctuated every half round matching the unrecorded area and the recorded area of the first information layer 2 as shown in FIG. 7. The varying quantity of the envelope of these reproduced signals was measured, and the first information layer 2 the envelope change rate was figured out with reference to the amplitude of the reproduced signals in the unrecorded area of. Further, with the reproduced signal amplitude in the unrecorded area of the first information layer 2 being represented by $A_1$ and the reproduced signal amplitude in its recorded area being represented by $A_2$, the change rate of the envelope was defined by the following equation:

$$\text{Change rate}=(A_1-A_2)/A_1$$

At the same time, the error rate of the reproduced signals was measured.

The results of measurement of the envelope change rate and the error rate are shown in Table 2.

TABLE 2

| Disk | Error rate | Change rate [%] |
|---|---|---|
| (1) | $2 \times 10^{-5}$ | 1 |
| (2) | $7 \times 10^{-5}$ | 5 |
| (3) | $6 \times 10^{-5}$ | 3 |
| (4) | $1 \times 10^{-3}$ | 4 |
| (5) | $8 \times 10^{-4}$ | 8 |
| (6) | $1 \times 10^{-3}$ | 10 |

While disks (1) through (3) gave satisfactory error rates, lower than the generally accepted threshold $1\times 10^{-4}$ for error rates, the error rates of disks (4) through (6) were not low enough.

The envelop change rate was satisfactory, no more than 5% for disks (1) through (4), but greater than that for disks (5) and (6).

When signals reproduced out of the second information layer 3 of each disk were measured within a reproduced signal processing circuit consisting of a binarizing circuit and a PLL (phase lock loop) circuit, the disks (4) through (6) were unstable in the operation of the binarizing circuit because of their large envelope fluctuations and the disks (4) through (6) were not stable in the operation of the PLL circuit on account of their inadequate reproduced signal quality.

These results are considered attributable to the following reasons. In the disks (1) through (3), conceivably, as the transmittance of the recorded area and the transmittance of the unrecorded area in the first information layer 2 vary little, the intensity of the laser beam reaching the second information layer 3 is varied little by the recording state of the first information layer 2, and the envelope varies little, resulting in stabilized binarizing operation and a reduced error rate. The results shown in Table 2 reveal the superiority of the disks (1), (2) and (3), and consequently Table 1 reveals that a satisfactory error rate or less than $1 \times 10^{-4}$ ratio is obtained when the absolute value of the transmittance ratio is not more than 10%.

In the disks (4) through (6), as the average transmittance of the first information layer 2 is low, the intensity of the laser beam reaching this information layer is less at the time of recording onto or reproducing out of the second information layer 3, conceivably resulting in deteriorated quality of reproduced signals and a higher error rate. The results shown in Table 2 reveal the inferiority of the disks (4), (5) and (6) and consequently Table 1 reveals that the error rate is not good enough, surpassing $1 \times 10^{-4}$, when the average transmittance is less than 40%.

From these findings, it was known that, because the disks (1) through (3) were reduced in the absolute value of the transmittance ratio $(T_c-T_a)/T_c$ to 10% or below and raised in the average transmittance $(T_a+T_c)/2$ of the first information layer 2 to 40% or above, information could be satisfactorily recorded onto and reproduced out of the second information layer 3.

Figure 4:
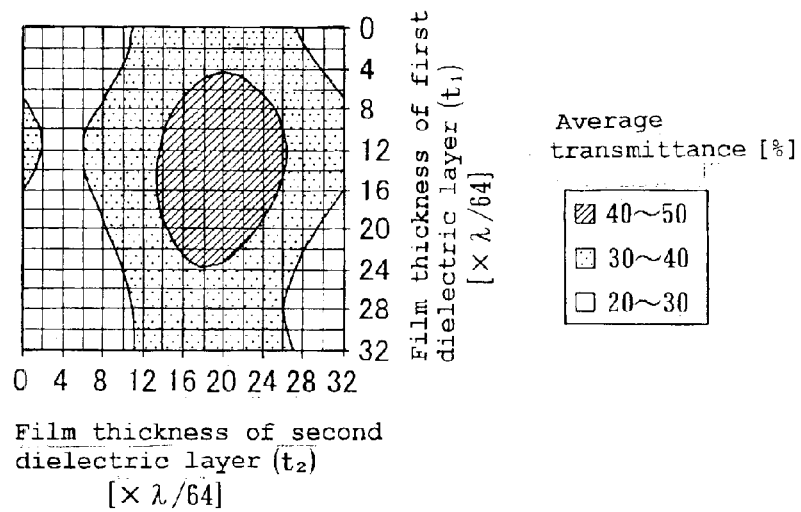
FIGS. 4(a) and 4(b) are diagrams showing the results of calculation of the average transmittance and the transmittance ratio in the first embodiment.
Figure 4:
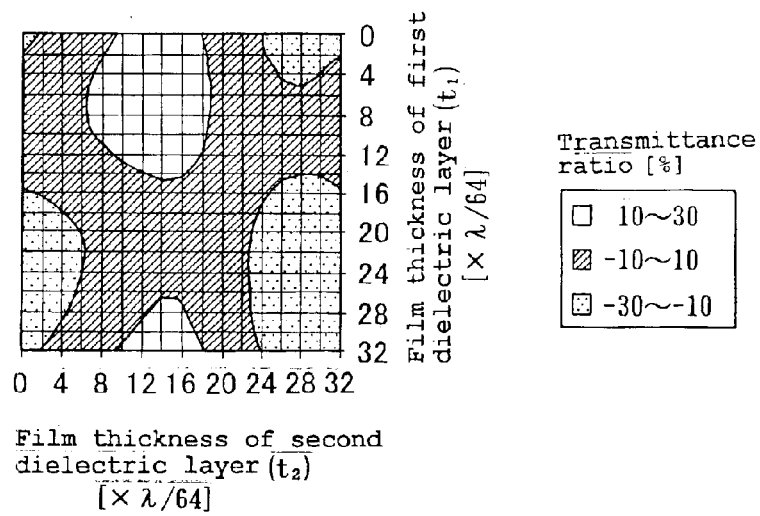

Furthermore, the film thickness conditions to enable the average transmittance $(T_a+T_c)/2$ to be raised to 40% or above and the absolute value of the transmittance ratio $(T_c-T_a)/T_c$ to be reduced to 10% or below in the configuration shown in FIG. 2 were checked in detail by calculation. FIGS. 4(a) and 4(b) are diagrams in which changes of the average transmittance $(T_a+T_c)/2$ and of the transmittance ratio $(T_c-T_a)/T_c$ are plotted where, by way of example, the thickness $t_a$ of the recording layer is set to 10 nm, the thickness $t_b$ of the reflecting layer is set to 10 nm and the film thickness $t_1$ of the first dielectric layer and the film thickness $t_2$ of the second dielectric layer are varied. In FIG. 4, the wavelength of the laser beam is set to 405 nm, and the film thicknesses of the upper dielectric and the lower dielectric are indicated in optical length with reference to the wavelength ($\lambda$) of the laser beam.

If the film thickness of the dielectric layer which gives an average transmittance $(T_a+T_c)/2$ of 40% or more in FIG. 4(a) and the film thickness of the dielectric layer which gives an absolute value of the transmittance ratio $(T_c-T_a)/T_c$ of 10% or less in FIG. 4(b) can be made compatible with each other, the combination of the film thicknesses of these recording layer and reflecting layer will enable the first information layer 2 to be configured so as to make possible satisfactory recording and reproduction of information onto and out of the second information layer 3.

Table 3 shows, when the film thickness $t_a$ of the recording layer is varied from 2 to 32 nm and the film thickness $t_b$ of the reflecting layer, from 2 to 36 nm, whether or not a first information layer 2 that has potential to keep the average transmittance $(T_a+T_c)/2$ at or above 40% and the absolute value of the transmittance ratio $(T_c-T_a)/T_c$ at or below 10% can be configured.

In the table, ○ marks indicate that the pertinent film thicknesses $t_a$ and $t_b$ can keep the average transmittance at or above 40% and the absolute value of the transmittance ratio at or below 10%. To add, × marks indicate that, whatever $t_a$ and $t_b$ maybe chosen, there is no possibility to keep the average transmittance at or above 40% and the absolute value of the transmittance ratio at or below 10%. In other words, there is no area whatsoever in which the average transmittance is from 40 to 50% and the transmittance ratio is from −10 to +10% in FIGS. 4(a) and 4(b).

If similar calculations to those referenced in FIG. 4(a) and FIG. 4(b) are done on every combination of individual recording layers and reflecting layers and, with the film thickness of the dielectric layer varied, a point where the average transmittance and the transmittance ratio are compatible is found, it will be regarded that a first information layer 2 satisfying the conditions can be configured.

TABLE 3

| $t_b$[nm] | $t_a$[nm] | | | | | | | | | | | | | | |
|---|---|---|---|---|---|---|---|---|---|---|---|---|---|---|---|
| | 2 | 4 | 6 | 8 | 10 | 12 | 14 | 16 | 18 | 20 | 22 | 24 | 26 | 28 | 30 | 32 |
| 2 | ○ | ○ | ○ | ○ | ○ | ○ | X | X | X | X | X | X | X | X | X | X |
| 4 | ○ | ○ | ○ | ○ | ○ | ○ | X | X | X | X | X | X | X | X | X | X |
| 6 | ○ | ○ | ○ | ○ | ○ | ○ | X | X | X | X | X | X | X | X | X | X |
| 8 | ○ | ○ | ○ | ○ | ○ | ○ | X | X | X | X | X | X | X | X | X | X |
| 10 | ○ | ○ | ○ | ○ | ○ | ○ | X | X | X | X | X | X | X | X | X | X |
| 12 | ○ | ○ | ○ | ○ | ○ | ○ | X | X | X | X | X | X | X | X | X | X |
| 14 | ○ | ○ | ○ | ○ | ○ | ○ | X | X | X | X | X | X | X | X | X | X |
| 16 | ○ | ○ | ○ | ○ | ○ | ○ | X | X | X | X | X | X | X | X | X | X |
| 18 | ○ | ○ | ○ | ○ | ○ | ○ | X | X | X | X | X | X | X | X | X | X |
| 20 | ○ | ○ | ○ | ○ | ○ | X | X | X | X | X | X | X | X | X | X | X |
| 22 | ○ | ○ | ○ | ○ | ○ | X | X | X | X | X | X | X | X | X | X | X |
| 24 | ○ | ○ | ○ | ○ | X | X | X | X | X | X | X | X | X | X | X | X |
| 26 | ○ | ○ | ○ | X | X | X | X | X | X | X | X | X | X | X | X | X |
| 28 | ○ | ○ | X | X | X | X | X | X | X | X | X | X | X | X | X | X |
| 30 | ○ | X | X | X | X | X | X | X | X | X | X | X | X | X | X | X |
| 32 | X | X | X | X | X | X | X | X | X | X | X | X | X | X | X | X |
| 34 | X | X | X | X | X | X | X | X | X | X | X | X | X | X | X | X |
| 36 | X | X | X | X | X | X | X | X | X | X | X | X | X | X | X | X |

This table reveals that a film thickness satisfying the following conditions provides a configuration that has potential to meet the requirements of 40% or more in the average transmittance and 10% or less in the absolute value of the transmittance ratio.

$t_a \leq 12$ when $t_b \leq 18$, $t_a \leq 10$ when $18 < t_b \leq 22$, and $t_a \leq 32 - t_b$ when $22 < t_b \leq 30$.

Table 3 also shows that a configuration meeting the above-stated requirements of the average transmittance and the transmittance ratio can be obtained with a configuration in which both the recording layer and the reflecting layer are thin. This means that the layers which have optical absorption in the first information layer 2 are mainly the recording layer and the reflecting layer. It can further be the that, since the recording layer is nearer than the reflecting layer as viewed from the light source side, the absorption index of the recording layer is greater than the absorption index of the reflecting layer and that increasing the film thickness of the recording layer can influence the transmittance more than increasing the film thickness of the reflecting layer.

Further, when the values of the absorption index $A_a$ of the recording layer in the amorphous state and the absorption index $A_c$ of the recording layer in the crystalline state were calculated for the disks (1) and (3), the result was $A_a > A_c$. This is because, since the reflectivities of (1) and (3) were set to be $R_a < R_c$, in order to reduce the absolute value of the transmittance ratio (i.e. to substantially equalize $T_c$ and $T_a$) configuration is made easier by giving a relationship of $A_a > A_c$ to the absorption index of the recording layer ($\leq 100\%$ –reflectivity–transmittance). Conversely, where the reflectivities are caused to be $R_a > R_c$ as in the case of the disk (2), a configuration satisfying the above-stated requirements can be readily obtained by giving the absorption index of the recording layer a relationship of $A_a < A_c$. Whereas relative magnitudes of $A_a$ and $A_c$ vary with the optical constants and the film thicknesses of the individual films constituting the information layers, if the optical constant of the recording film in the amorphous state is set to be $n_a - ik_a$ and the optical constant in the crystalline state, $n_c - ik_c$, it is easier to obtain a configuration in which $T_c$ and $T_a$ are substantially equalized by having $A_a > A_c$ as the absorption indices of the recording films and $R_a < R_c$ as the reflectivities, where:

$$n_a + k_a < n_c + k_c.$$

Conversely, where:

$$n_a + k_a > n_c + k_c$$

it tends to be easier to obtain a configuration in which $T_c$ and $T_a$ are substantially equalized by having $A_a < A_c$ as the absorption indices of the recording films and $R_a > R_c$ as the reflectivities.

Incidentally, as the recording layer in the previous described embodiment has a relationship $n_a + k_a < n_c + k_c$, it is easier to obtain a configuration in which $T_c$ and $T_a$ are substantially equalized by having $A_a > A_c$ as the absorption indices of the recording films and $R_a < R_c$ as the reflectivities.

To sum up the foregoing, whatever the optical constant may be, it is desirable for the relative magnitudes of $T_a$ and $T_c$ matching the relative magnitudes of $R_a$ and $R_c$ in the amorphous state to differ from the relative magnitudes of $T_a$ and $T_c$ matching the relative magnitudes of $R_a$ and $R_c$ in the crystalline state.

As so far described, in the optical information recording medium in this embodiment, by reducing the absolute value of the transmittance ratio $(T_c - T_a)/T_c$ to 10% or less and raising the average transmittance $(T_a + T_c)/2$ of the first information layer 2 to 40% or more, sufficient intensity of the laser beam is enabled to reach the second information layer 3, and information can be accurately recorded and reproduced irrespective of whether or not information is recorded on the first information layer 2.

(Second Embodiment)

Figure 5:
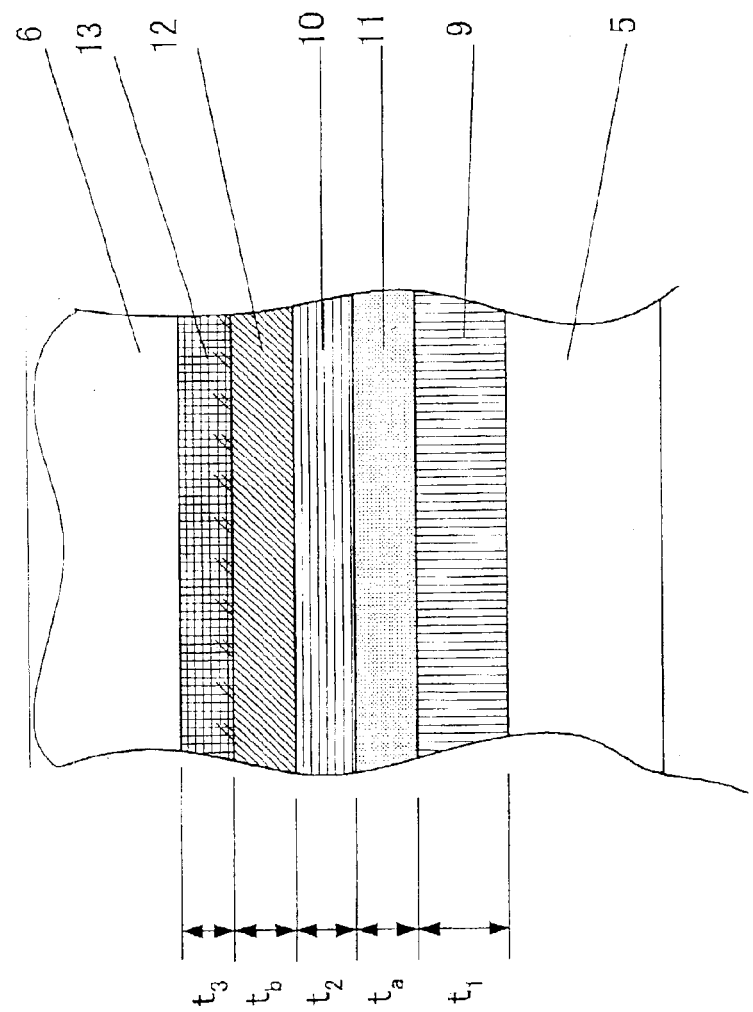
FIG. 5 is a section of a first information layer in the second embodiment.
Figure 6:
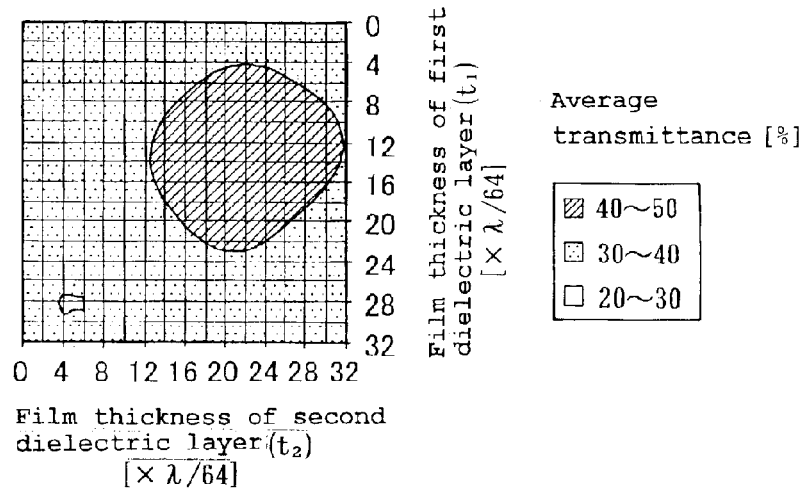
FIGS. 6(a) and 6(b) are diagrams showing the results of calculation of the average transmittance and the transmittance ratio in the second embodiment.
Figure 6:
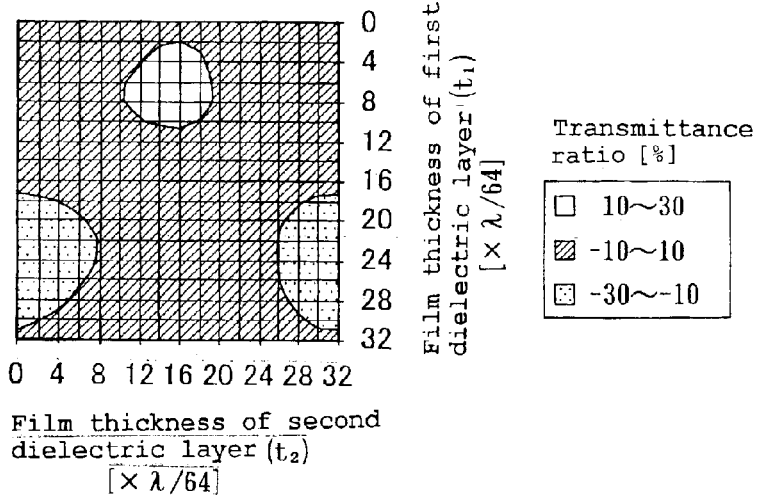

FIG. 5 is a sectional view showing an example of configuration of the first information layer 2, which constitutes the nearer information layer in FIG. 1 as viewed from the incidence side of the laser beam. This mode differs from the first embodiment in that a third dielectric layer 13 is provided over the reflecting layer 12. FIG. 6 is a diagram in which changes of the average transmittance $(T_a + T_c)/2$ and of the transmittance ratio $(T_c - T_a)/T_c$ are plotted where the thickness of the recording layer is set to 10 nm, the thickness of the reflecting layer is set to 10 nm, the thickness of the third dielectric layer is set to 10 nm and the film thicknesses of the first dielectric layer and the second dielectric layer are varied. To compare FIG. 6 with FIG. 4, in spite of the same thicknesses of the recording layer and of the reflecting layer, the provision of the third dielectric layer has expanded the area in which the absolute value of the transmittance ratio $(T_c - T_a)/T_c$ is 10% or less. Further, if the thickness of the third dielectric layer is selected properly, it will also be possible to enhance the average transmittance. Thus, this has the role of increasing the freedom of configuration of the first information layer 2.

Table 4 shows an example of film thickness configuration of the first information layer 2 of a disk produced on a trial basis in this embodiment, its calculated transmittances in the amorphous state ($T_a$) and in the crystalline state ($T_c$) reflectivities in the amorphous state ($R_a$) and the crystalline state ($R_c$), absorption indices in the amorphous state ($A_a$) and in the crystalline state ($A_c$), transmittance ratio between the amorphous state and the crystalline state $(T_c - T_a)/T_c$, and average transmittance $(T_a + T_c)/2$.

TABLE 4

| Disk | $t_a$ [nm] | $t_b$ [nm] | $t_1$ [nm] | $t_2$ [nm] | $t_3$ [nm] | $R_c$ [%] | $R_a$ [%] | $T_c$ [%] | $T_a$ [%] | $A_c$ [%] | $A_a$ [%] | Transmittance ratio [%] | Average transmittance [%] |
|---|---|---|---|---|---|---|---|---|---|---|---|---|---|
| (7) | 8 | 10 | 40 | 22 | 30 | 7 | 0 | 41 | 40 | 47 | 56 | 2 | 41 |
| (8) | 6 | 8 | 68 | 12 | 10 | 15 | 5 | 44 | 46 | 35 | 44 | −4 | 45 |
| (9) | 5 | 10 | 62 | 28 | 50 | 12 | 2 | 41 | 42 | 42 | 53 | −3 | 42 |
| (10) | 6 | 26 | 50 | 59 | 50 | 21 | 28 | 45 | 38 | — | — | 15 | 41 |
| (11) | 10 | 30 | 34 | 68 | 70 | 27 | 35 | 33 | 36 | — | — | −10 | 34 |
| (12) | 8 | 28 | 68 | 50 | 70 | 13 | 31 | 29 | 21 | — | — | 28 | 25 |

In this embodiment, as shown in Table 4, disks differing in transmittance ratio and average transmittance of the first information layer 2 were prepared by varying the thickness $t_a$ of the recording layer, the thickness $t_b$ of the reflecting layer, the thickness $t_1$ of the first dielectric layer, the thickness $t_2$ of the second dielectric layer, and the thickness $t_3$ of the third dielectric layer.

The disks were prepared in a similar way to those in the first embodiment, differing from the first embodiment in the following respects. As the first information layer 2, there were formed in succession a third dielectric layer of ZnS—SiO$_2$ to $t_3$ nm, a reflecting layer of AgPdCu to $t_b$ nm, a second dielectric layer of ZnS—SiO$_2$ to $t_2$ nm, a recording layer of GeSbTe to $t_a$ nm, and a first dielectric layer of ZnS—SiO$_2$ to $t_1$ nm.

Then, a recording/reproducing test was carried out using the six different disks shown in Table 3. As in the first embodiment, each disk was turned at a linear speed of 5 m/s, either one of the information layers 2 and 3 of the disk was irradiated with a semiconductor laser beam of 405 nm in wavelength, narrowed down with an objective lens of 0.85 in numerical aperture (NA).

The results of measurement of the envelope change rate and the error rate are shown in Table 5.

TABLE 5

| Disk | Error rate | Change rate [%] |
|---|---|---|
| (7) | $6 \times 10^{-5}$ | 1 |
| (8) | $3 \times 10^{-5}$ | 2 |
| (9) | $6 \times 10^{-5}$ | 2 |
| (10) | $1 \times 10^{-3}$ | 8 |
| (11) | $5 \times 10^{-4}$ | 5 |
| (12) | $4 \times 10^{-3}$ | 14 |

While disks (7) through (10) gave satisfactory error rates, lower than the generally accepted threshold $1 \times 10^{-4}$ for error rates, the error rates of disks (10) through (12) were not low enough. The envelop change rate was satisfactory, no more than 5% for disks (7) through (9) and (11), but greater than that for disks (10) and (12).

When signals reproduced out of the second information layer 3 of each disk were measured within a reproduced signal processing circuit consisting of a binarizing circuit and a PLL (phase lock loop) circuit, the disks (11) and (12) were unstable in the operation of the binarizing circuit because of their large envelope fluctuations, manifesting high error rates. The disks (10) through (12) were not stable in the operation of the PLL on account of their inadequate reproduced signal quality, which contributed to raising error rates.

The results shown in Table 4 and Table 5 reveal that low enough error rates are obtained, less than $1 \times 10^{-4}$, when the absolute value of the transmittance ratio is not more than 10% and the average transmittance is not less than 40%.

From these findings, it was known that, because the disks (7) through (9) were raised in the average transmittance $(T_a+T_c)/2$ of the first information layer 2 to 40% or above and reduced in the absolute value of the transmittance ratio $(T_c-T_a)/T_c$ to 10% or below, information could be satisfactorily recorded onto and reproduced out of the second information layer 3.

Furthermore, the film thickness conditions to enable the average transmittance $(T_a+T_c)/2$ to be raised to 40% or above and the absolute value of the transmittance ratio $(T_c-T_a)/T_c$ to be reduced to 10% or below in the configuration shown in FIG. 5 were checked in detail by calculation.

Table 6 shows, when the film thickness $t_a$ of the recording layer is varied from 2 to 32 nm and the film thickness $t_b$ of the reflecting layer, from 2 to 36 nm, whether or not a first information layer 2 that has potential to keep the average transmittance $(T_a+T_c)/2$ at or above 40% and the absolute value of the transmittance ratio $(T_c-T_a)/T_c$ at or below 10% can be configured. Further, Table 7 shows a case in which the film thicknesses of the recording layer and of the reflecting layer were similarly varied and the film thickness $t_3$ of the third dielectric layer was set to 30 nm; Table 8, a similar case in which the thickness was 50 nm, and Table 9, another case in which the thickness was 70 nm.

TABLE 6

$t_3 = 10[nm]$

| $t_b[nm]$ | $t_a[nm]$ | | | | | | | | | | | | | | | |
|---|---|---|---|---|---|---|---|---|---|---|---|---|---|---|---|---|
| | 2 | 4 | 6 | 8 | 10 | 12 | 14 | 16 | 18 | 20 | 22 | 24 | 26 | 28 | 30 | 32 |
| 2 | ○ | ○ | ○ | ○ | ○ | ○ | X | X | X | X | X | X | X | X | X | X |
| 4 | ○ | ○ | ○ | ○ | ○ | ○ | X | X | X | X | X | X | X | X | X | X |
| 6 | ○ | ○ | ○ | ○ | ○ | ○ | X | X | X | X | X | X | X | X | X | X |
| 8 | ○ | ○ | ○ | ○ | ○ | ○ | X | X | X | X | X | X | X | X | X | X |
| 10 | ○ | ○ | ○ | ○ | ○ | ○ | X | X | X | X | X | X | X | X | X | X |
| 12 | ○ | ○ | ○ | ○ | ○ | ○ | X | X | X | X | X | X | X | X | X | X |
| 14 | ○ | ○ | ○ | ○ | ○ | ○ | X | X | X | X | X | X | X | X | X | X |
| 16 | ○ | ○ | ○ | ○ | ○ | ○ | X | X | X | X | X | X | X | X | X | X |
| 18 | ○ | ○ | ○ | ○ | ○ | ○ | X | X | X | X | X | X | X | X | X | X |
| 20 | ○ | ○ | ○ | ○ | ○ | X | X | X | X | X | X | X | X | X | X | X |
| 22 | ○ | ○ | ○ | ○ | ○ | X | X | X | X | X | X | X | X | X | X | X |
| 24 | ○ | ○ | ○ | ○ | ○ | X | X | X | X | X | X | X | X | X | X | X |
| 26 | ○ | ○ | ○ | ○ | X | X | X | X | X | X | X | X | X | X | X | X |
| 28 | ○ | ○ | ○ | ○ | X | X | X | X | X | X | X | X | X | X | X | X |
| 30 | ○ | ○ | ○ | X | X | X | X | X | X | X | X | X | X | X | X | X |
| 32 | ○ | X | X | X | X | X | X | X | X | X | X | X | X | X | X | X |
| 34 | X | X | X | X | X | X | X | X | X | X | X | X | X | X | X | X |
| 36 | X | X | X | X | X | X | X | X | X | X | X | X | X | X | X | X |

TABLE 7

$t_3 = 30[nm]$

| $t_b[nm]$ | $t_a[nm]$ | | | | | | | | | | | | | | | |
|---|---|---|---|---|---|---|---|---|---|---|---|---|---|---|---|---|
| | 2 | 4 | 6 | 8 | 10 | 12 | 14 | 16 | 18 | 20 | 22 | 24 | 26 | 28 | 30 | 32 |
| 2 | ○ | ○ | ○ | ○ | ○ | ○ | X | X | X | X | X | X | X | X | X | X |
| 4 | ○ | ○ | ○ | ○ | ○ | ○ | X | X | X | X | X | X | X | X | X | X |
| 6 | ○ | ○ | ○ | ○ | ○ | ○ | X | X | X | X | X | X | X | X | X | X |
| 8 | ○ | ○ | ○ | ○ | ○ | ○ | X | X | X | X | X | X | X | X | X | X |

TABLE 7-continued $t_3 = 30[nm]$

| $t_b[nm]$ | $t_a[nm]$ | | | | | | | | | | | | | | | |
|---|---|---|---|---|---|---|---|---|---|---|---|---|---|---|---|---|
| | 2 | 4 | 6 | 8 | 10 | 12 | 14 | 16 | 18 | 20 | 22 | 24 | 26 | 28 | 30 | 32 |
| 10 | ○ | ○ | ○ | ○ | ○ | ○ | X | X | X | X | X | X | X | X | X | X |
| 12 | ○ | ○ | ○ | ○ | ○ | ○ | X | X | X | X | X | X | X | X | X | X |
| 14 | ○ | ○ | ○ | ○ | ○ | ○ | X | X | X | X | X | X | X | X | X | X |
| 16 | ○ | ○ | ○ | ○ | ○ | ○ | X | X | X | X | X | X | X | X | X | X |
| 18 | ○ | ○ | ○ | ○ | ○ | ○ | X | X | X | X | X | X | X | X | X | X |
| 20 | ○ | ○ | ○ | ○ | ○ | ○ | X | X | X | X | X | X | X | X | X | X |
| 22 | ○ | ○ | ○ | ○ | ○ | ○ | X | X | X | X | X | X | X | X | X | X |
| 24 | ○ | ○ | ○ | ○ | ○ | ○ | X | X | X | X | X | X | X | X | X | X |
| 26 | ○ | ○ | ○ | ○ | ○ | X | X | X | X | X | X | X | X | X | X | X |
| 28 | ○ | ○ | ○ | ○ | ○ | X | X | X | X | X | X | X | X | X | X | X |
| 30 | ○ | ○ | ○ | ○ | X | X | X | X | X | X | X | X | X | X | X | X |
| 32 | ○ | ○ | ○ | X | X | X | X | X | X | X | X | X | X | X | X | X |
| 34 | ○ | X | X | X | X | X | X | X | X | X | X | X | X | X | X | X |
| 36 | X | X | X | X | X | X | X | X | X | X | X | X | X | X | X | X |

TABLE 8

$t_3 = 50[nm]$

| $t_b[nm]$ | $t_a[nm]$ | | | | | | | | | | | | | | | |
|---|---|---|---|---|---|---|---|---|---|---|---|---|---|---|---|---|
| | 2 | 4 | 6 | 8 | 10 | 12 | 14 | 16 | 18 | 20 | 22 | 24 | 26 | 28 | 30 | 32 |
| 2 | ○ | ○ | ○ | ○ | ○ | ○ | ○ | X | X | X | X | X | X | X | X | X |
| 4 | ○ | ○ | ○ | ○ | ○ | ○ | ○ | X | X | X | X | X | X | X | X | X |
| 6 | ○ | ○ | ○ | ○ | ○ | ○ | ○ | X | X | X | X | X | X | X | X | X |
| 8 | ○ | ○ | ○ | ○ | ○ | ○ | ○ | X | X | X | X | X | X | X | X | X |
| 10 | ○ | ○ | ○ | ○ | ○ | ○ | ○ | X | X | X | X | X | X | X | X | X |
| 12 | ○ | ○ | ○ | ○ | ○ | ○ | ○ | X | X | X | X | X | X | X | X | X |
| 14 | ○ | ○ | ○ | ○ | ○ | ○ | ○ | X | X | X | X | X | X | X | X | X |
| 16 | ○ | ○ | ○ | ○ | ○ | ○ | X | X | X | X | X | X | X | X | X | X |
| 18 | ○ | ○ | ○ | ○ | ○ | ○ | X | X | X | X | X | X | X | X | X | X |
| 20 | ○ | ○ | ○ | ○ | ○ | ○ | X | X | X | X | X | X | X | X | X | X |
| 22 | ○ | ○ | ○ | ○ | ○ | X | X | X | X | X | X | X | X | X | X | X |
| 24 | ○ | ○ | ○ | ○ | X | X | X | X | X | X | X | X | X | X | X | X |
| 26 | ○ | ○ | ○ | X | X | X | X | X | X | X | X | X | X | X | X | X |
| 28 | ○ | ○ | X | X | X | X | X | X | X | X | X | X | X | X | X | X |
| 30 | X | X | X | X | X | X | X | X | X | X | X | X | X | X | X | X |
| 32 | X | X | X | X | X | X | X | X | X | X | X | X | X | X | X | X |
| 34 | X | X | X | X | X | X | X | X | X | X | X | X | X | X | X | X |
| 36 | X | X | X | X | X | X | X | X | X | X | X | X | X | X | X | X |

TABLE 9

$t_3 = 70[nm]$

| $t_b[nm]$ | $t_a[nm]$ | | | | | | | | | | | | | | | |
|---|---|---|---|---|---|---|---|---|---|---|---|---|---|---|---|---|
| | 2 | 4 | 6 | 8 | 10 | 12 | 14 | 16 | 18 | 20 | 22 | 24 | 26 | 28 | 30 | 32 |
| 2 | ○ | ○ | ○ | ○ | ○ | ○ | ○ | X | X | X | X | X | X | X | X | X |
| 4 | ○ | ○ | ○ | ○ | ○ | ○ | ○ | X | X | X | X | X | X | X | X | X |
| 6 | ○ | ○ | ○ | ○ | ○ | ○ | ○ | X | X | X | X | X | X | X | X | X |
| 8 | ○ | ○ | ○ | ○ | ○ | ○ | ○ | X | X | X | X | X | X | X | X | X |
| 10 | ○ | ○ | ○ | ○ | ○ | ○ | ○ | X | X | X | X | X | X | X | X | X |
| 12 | ○ | ○ | ○ | ○ | ○ | ○ | ○ | X | X | X | X | X | X | X | X | X |
| 14 | ○ | ○ | ○ | ○ | ○ | ○ | X | X | X | X | X | X | X | X | X | X |
| 16 | ○ | ○ | ○ | ○ | ○ | ○ | X | X | X | X | X | X | X | X | X | X |
| 18 | ○ | ○ | ○ | ○ | ○ | ○ | X | X | X | X | X | X | X | X | X | X |
| 20 | ○ | ○ | ○ | ○ | ○ | X | X | X | X | X | X | X | X | X | X | X |
| 22 | ○ | ○ | ○ | ○ | X | X | X | X | X | X | X | X | X | X | X | X |
| 24 | ○ | ○ | ○ | X | X | X | X | X | X | X | X | X | X | X | X | X |
| 26 | ○ | X | X | X | X | X | X | X | X | X | X | X | X | X | X | X |
| 28 | X | X | X | X | X | X | X | X | X | X | X | X | X | X | X | X |
| 30 | X | X | X | X | X | X | X | X | X | X | X | X | X | X | X | X |
| 32 | X | X | X | X | X | X | X | X | X | X | X | X | X | X | X | X |
| 34 | X | X | X | X | X | X | X | X | X | X | X | X | X | X | X | X |
| 36 | X | X | X | X | X | X | X | X | X | X | X | X | X | X | X | X |

These tables reveal that a film thickness satisfying the following conditions provides a configuration that meets the aforementioned requirements about the average transmittance and the transmittance ratio if the recording layer is made $t_a$[nm] thick and the metallic reflecting layer $t_b$[nm] thick irrespective of whatever the film thickness of the third dielectric layer is between 10 and 70 nm:

$t_b \leq 12$ when $t_b \leq 18$, $t_a \leq 38 - t_a$ when $16 < t_a \leq 18$ $t_a \leq 10$ when $18 < t_a \leq 20$ $t_a \leq 30 - t_a$ when $20 < t_a \leq 24$ and $t_a \leq 28 - t_a$ when $24 < t_a \leq 26$.

As is seen from Table 6 through Table 9, a configuration meeting the above-stated requirements of the average transmittance and the transmittance ratio can be obtained with a configuration in which both the recording layer and the reflecting layer are thin. This means that the layers which have optical absorption in the first information layer 2 are mainly the recording layer and the reflecting layer.

Further, when the values of the absorption index $A_a$ of the recording layer in the amorphous state and the absorption index $A_c$ of the recording layer in the crystalline state were calculated for the disks (7) through (9), the result was $A_a > A_c$. This is because, since the reflectivities of (7) through (9) were set to be $R_a < R_c$, in order to reduce the absolute value of the transmittance ratio (i.e. to substantially equalize $T_c$ and $T_a$) configuration is made easier by giving a relationship of $A_a > A_c$ to the absorption index of the recording layer ($\leq 100\%$-reflectivity-transmittance).

As hitherto described, the optical information recording medium in this embodiment as well, if so configured as to reduce the absolute value of the transmittance ratio $(T_c - T_a)/T_c$ to 10% or below and raise the average transmittance $(T_a + T_c)/2$ of the first information layer 2 to 40% or above, sufficient intensity of the laser beam will be enabled to reach the second information layer 3, and information can be accurately recorded and reproduced irrespective of whether or not information is recorded on the first information layer 2.

Finally, whereas the aforementioned transmittances $T_a$ and $T_c$ are usually measured with an optical instrument, such as a spectroscope, it is made easier to measure the difference between $T_c$ and $T_a$ by utilizing reproduced signals obtained when the second information layer is irradiated with an information reproducing laser beam as shown in FIG. 7. Such an optical measuring method will be described anew with reference to a drawing.

FIG. 9 are schematic diagrams illustrating such a first optical measuring method of the present invention, in which the upper part comprises schematic sections showing how the laser beam irradiates each information layer and the lower part, a waveform diagram of a reproduced signal obtained from the laser beam reflected by the second information layer.

(Step 1)

First, in a state in which nothing is recorded on the first information layer as shown in the upper part of FIG. 9(a), irradiation with a laser beam is carried out with focus on the second information layer. It is desirable for the irradiating position in this process to be set in a so-called still state, in which a return to the original position takes place, for instance, at every full turn, because in this way comparison with the result of measurement at the next step is facilitated.

The reflected intensity is converted into an electric current or a voltage by a photodetector for signal reproduction or the like, and observed as a reproduced waveform of a substantially direct current as shown in the lower part of FIG. 9(a). Although the actual waveform is more or less uneven because its is fluctuated by the reflectivity of the optical disk or the like, it can be considered a D.C. waveform when averaged over time. The zero level of the longitudinal axis of this diagram represents the output of the photodetector when the optical disk is removed from the optical path of the laser beam. Therefore, level $S_a$ shown in the diagram represents the reflected intensity in a state in which nothing is recorded on the first information layer.

(Step 2)

Next, random signals or monotone signals are recorded in a position on the first information layer immediately below the position in which $S_a$ was measured at step 1 as shown in the upper part of FIG. 9(b). The recording range is designated to include the whole area which, when a laser beam is focused on the second information layer, the laser beam passes the first information layer. If the wavelength of the laser beam is 405 nm, the NA of the objective lens is 0.85, the thickness of the middle layer is 30 μm, and the refractive index of the middle layer is 1.60, the diameter of the laser beam in the first information layer will be approximately 37.6 μm. With this diameter and the eccentricity between the first and second layers taken into consideration, the required recording range may be 200 μm or so.

(Step 3)

Finally, irradiation with the laser beam is carried out with focus on the second information layer through the first information layer on which random signals or monotone signals are recorded as shown in the upper part of FIG. 9(c). It is desirable with a view to greater accuracy of measurement for the irradiating position then to coincide with the track measured at step 1. The reflected intensity is observed as a reproduced waveform of a substantially direct current as shown in the lower part of FIG. 9(c). Level $S_b$ shown in the diagram represents the reflected intensity in a recorded of the first information layer. This diagram shows a case in which the transmittance is lower in the recorded state than in the unrecorded state.

(Step 4)

From $S_a$ and $S_b$, the difference in transmittance between the unrecorded state and the recorded state of the first information layer can be figured out by the following calculation. Thus, where α is the ratio of the area of recording marks to the whole sectional area of the laser beam in the section of the laser beam on the first information layer when the laser beam is focused on the second information layer, the equivalent transmittance $T_a'$ of the recorded first information layer is:

$$T_a' = (1-\alpha)T_c + \alpha T_a = T_c - \alpha(T_c - T_a)$$

Since the transmittance of the unrecorded first information layer remains $T_c$ and the laser beam is transmitted by the first information layer twice according to the measurements of $S_a$ and $S_b$, the following equation holds:

$$S_b/S_a = (T_a'/T_c)^2$$

These two equations show that the aforementioned transmittance ratio can be obtained from:

$$(T_c - T_a)/T_c = (1 - (S_b/S_a)^{1/2})/\alpha \qquad \text{Equation (1)}$$

The value of α usually is approximately 0.25, though it is varied by recording conditions including the recording power.

By these steps 1 through 4, changes in transmittance between the unrecorded state and the recorded state of the first information layer can be easily measured without having to use a special measuring instrument.

FIGS. 10 are schematic diagrams showing the procedure of a second optical measuring method, in which the upper part comprises schematic sections showing how the laser beam irradiates each information layer and the lower part, a waveform diagram of a reproduced signal obtained from the laser beam reflected by the second information layer.

(Step 1)

First, in a state in which nothing is recorded on the first information layer as shown in the upper part of FIG. 10(a), irradiation with a laser beam is carried out with focus on the second information layer, random or monotone signals are recorded on a predetermined track of the second information layer. Then the signals recorded on that track are irradiated with a laser beam of the reproduction level, converted into an electric current or a voltage by a photodetector or the like, and observed as an envelope waveform having a fixed amplitude as shown in the lower part of FIG. 10(a). The amplitude $A_1$ shown in the diagram represents the reproduced signal amplitude in a state in which nothing is recorded on the first information layer.

(Step 2)

Next, the random signals or monotone signals are recorded in a position on the first information layer immediately below the position in which $A_1$ was measured at step 1 as shown in the upper part of FIG. 10(b). The recording range is the same as according the first optical measuring method.

(Step 3)

Finally, irradiation with the laser beam is carried out with focus on the second information layer through the first information layer on which random signals or monotone signals are recorded as shown in the upper part of FIG. 10(c). The irradiating position then is caused to coincide with the track measured at step 1. The reproduced signals are observed as an envelope waveform having a fixed amplitude as shown in the lower part of FIG. 10(c). The amplitude $A_2$ shown in the diagram represents the reproduced signal amplitude in the recorded state of the first information layer. This diagram, too, shows a case in which the transmittance is lower in the recorded state than in the unrecorded state of the first information layer.

(Step 4)

By replacing $S_a$ with $A_1$ and $S_b$ with $A_2$ in the calculation shown according to the first optical measuring method, the transmittance ratio $(T_c-T_a)/T_c$ between the unrecorded state and the recorded state of the first information layer can be figured out.

By these steps 1 through 4, changes in transmittance between the unrecorded state and the recorded state of the first information layer can be easily measured without having to use a special measuring instrument. Also, since the method described with reference to FIG. 10 uses reproduced amplitudes $A_1$ and $A_2$ for comparing the levels of reflected intensity, even if part of the reflected beam from the first information layer goes astray and comes incident on the photodetector, the difference in transmittance can be measured with greater accuracy because the stray light would be cancelled when the amplitudes are measured. On the other hand, by the method described with reference to FIG. 9 as well, if the size of the photodetector is made sufficiently small and the stray intensity is suppressed to, for instance, about 2% of the total incident intensity, the tolerance of the transmittance difference that is measured can be suppressed to $2/100$, making possible sufficiently accurate measurement.

Meanwhile as for the second optical measuring method of the present invention, as described in FIG. 11, a transmittance ratio $(|T_c-T_a|/T_c)$ between the recorded state and unrecorded state of the first information layer can be obtained in such manner that the differences $A_{1'}$ and $A_{2'}$ between the zero level and upper envelope of the modulation amplitude are detected and the $S_a$ is replaced with $A_{1'}$ and $S_b$ is replaced with $A_{2'}$ in the calculation described in the first optical measuring method description.

By using the optical measuring methods described so far, the transmittance ratio can be easily figured out through Equation (1). Since the desirable transmittance ratio of the first information layer is 10% or less, if Equation (1) is used, it will be satisfactory for $S_a$ and $S_b$ that are obtained by the first optical measuring method to meet the requirement of:

$$0 \leq |1-(S_b/S_a)^{1/2}| \leq 0.1\alpha.$$

Or it will be satisfactory for $A_1$ and $A_2$ obtained by the second optical measuring method to meet the requirement of:

$$0 \leq |1-(A_2/A_1)^{1/2}| \leq 0.1\alpha.$$

To add, although the first information layer 2 is configured of four layers as shown in FIG. 2 or five layers as shown in FIG. 5 in the media of the above-described modes of implementation, a multi-layered configuration having an interface layer between each adjacent pair of these layers can also be used if it is so structure as to satisfy the above-stated conditions regarding the transmittance ratio and/or the average transmittance. Some other configurations than those illustrated in FIG. 2 and FIG. 5, such as having no reflecting layer, can be used as well. Nor are the materials of the individual layers limited to those used in these modes of implementation.

Figure 8:
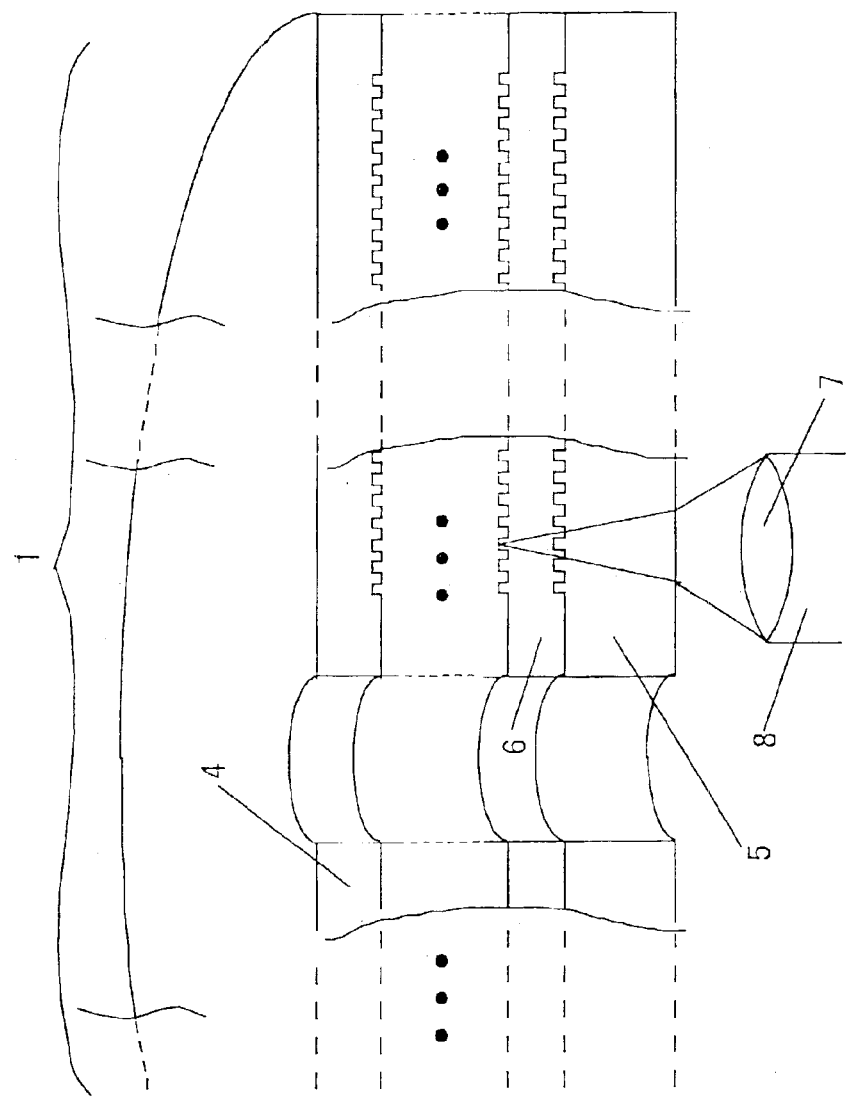
FIG. 8 is an external view and a section of an optical information recording medium in another mode of implementing the present invention.

While each optical disk in the above-described modes of implementation has two information layers, it is also acceptable for each disk to have three or more information layers as shown in FIG. 8, and to have a nearer positioned information layer than the farthest information layer as viewed from the incidence side of the laser beam satisfy the above-stated requirement regarding the transmittance ratio.

This synthesized transmittance is the product of the transmittances of the information layers. There exist, depending on the combination of the recorded and unrecorded states of different layers, a state in which the synthesized transmittance is at its minimum (this transmittance is represented by $T_{min}$) and a state in which it is at its maximum (this transmittance is represented by $T_{max}$). Similar to the case in which there are two information layers, in order to reduce the variations of the intensity of the laser beam reaching any information layer farther than this plurality of information layers, the configuration can be:

$$0 \leq |T_c-T_{min}|/T_c \leq 0.1 \text{ and } 0 \leq |T_c-T_{max}|/T_c \leq 0.1$$

where $T_c$ is the synthesized transmittance when every one of the plurality of information layers is in an unrecorded state.

In this case, since all the nearer positioned information layers may not necessarily secure an average transmittance of 40% or more, the S/N ratio of the reproduction circuit should be enhanced in order to ensure adequate signal quality.

Further in the optical measuring methods described above, The medium to be detected can has three or more information layers. In such case maximum change of the transmittance for the nearer plurality of the information layers can be detected by detecting the respective reflection amounts of case (a) and case (b). Here the case (a) means that the synthesized transmittance of the plurality of information layers positioned nearer than the farthest information layer from the incidence side of said laser beam, is minimum. The case (b) means that the synthesized transmittance of the plurality of information layers positioned nearer than the farthest information layer from the incidence side of said laser beam, is maximum.

And in the optical measuring method described above, the transmittance ratio is calculated in the step 4 on the basis of the measured $S_a$(or $A_1$, $A_1'$) and $S_b$ (or $A_2$, $A_2'$). But instead of it, by detecting the changing of such measured values the goodness of the change of the transmittance of the nearer positioned information layer can be easily obtained without measuring the transmission foctor ratio.

For example as parameters representing the changing of the signals, $(S_a-S_b)/S_a$ or $(A_1-A_2)/A_1$ or $(A_1'-A_2')/A_1'$ is defined. By obtaining such parameters, the amount of the effect which is caused by the nearer information layer against the quality of the reproduced signal of the farthest information layer, can be estimated without getting the transmittance ratio $(T_c-T_a)/T_c$. Then the goodness of the transmittance changing of the nearer information layer can be easily judged.

Meanwhile in the practical measuring condition, the $S_a$ (or $A_1, A_1'$) and $S_b$ (or $A_2, A_2'$) vary because of the unevenness of the reflectivities etc. of the disk, however the changing of the transmittance of the nearer information layer effect largely against the varying of the parameters.

Therefore even if the above parameters are obtained by recording locally signals on the nearer information layer, measuring the changing of the amount of the reflected beam from the farthest information layer via the nearer information layer and detecting maximum value as $S_a$ and minimum value as $S_b$, there is no problem for judging the goodness of the changing of the transmittance of the nearer information layer. As for the modulation amplitude $A_1, A_1', A_2, A_2'$ there is no problem as like.

Furthermore, the modulation system and recording density usable in the above-described modes of implementation are not limited to those described above, but it goes without saying that can be in any appropriate forms for the medium itself or the recording/reproducing apparatus.

As described so far, the optical information recording medium in the present invention can cause sufficient intensity of the laser beam to reach the information layer farther inside, and can accurately record and reproduce onto and out of the farther information layer irrespective of whether or not any information is recorded on the nearer information layer.

And, the optical measuring method of the present invention can easily detect the changing of the transmittance of the nearer information layer in such conditions of recorded or unrecorded.

What is claimed is:

1. An optical information recording medium having two information layers, converged irradiation of a laser beam onto any of said information layers causing information signals to be recorded or reproduced, wherein:

an information layer positioned nearer than the farthest information layer from the incidence side of said laser beam have a recording layer varying between two optically detectable states, the optical information recording medium having a configuration of:

$$0 \leq |T_c-T_a|/T_c \leq 0.1$$

where $T_c$ is the transmittance of said nearer positioned information layer when said recording layer is in state (a), and $T_a$ is the transmittance of the same when said recording layer is in state (b).

2. An optical information recording medium having three or more information layers, converged irradiation of any of which with a laser beam causes information signals to be recorded or reproduced, characterized in that:

each of a plurality of information layers positioned nearer than the farthest information layer from the incidence side of said laser beam has a recording layer varying between two optically detectable states, the optical information recording medium having a configuration of:

$$0 \leq |T_c-T_{min}|/T_c \leq 0.1 \text{ and } 0 \leq |T_c-T_{max}|/T_c \leq 0.1$$

where $T_c$ is a synthesized transmittance of said plurality of information layers when every one of the respective recording layers of said plurality of information layer in state (a);

$T_{min}$ is a minimum value of the synthesized transmittances which are derived from combinations of said various states of the respective recording layers, and $T_{max}$ is a maximum value of the synthesized transmittances which are derived from combinations of said various states of the respective recording layers.

3. The optical information recording medium, as set forth in claim 1, further having a configuration of:

$$(T_a+T_c)/2 \geq 0.4.$$

4. The optical information recording medium, as set forth in either claim 1 or 3, having a configuration of:

$A_c < A_a$ and $R_c > R_a$, or $A_c > A_a$ and $R_c < R_a$ where $A_c[\%]$ the absorption index of said recording layer of an information layer positioned nearer than the farthest information layer from the incidence side of said laser beam when said recording layer is in state (a), and $A_a[\%]$ is the absorption index of the same when said recording layer is in state (b), and $R_c[\%]$ is the reflectivity of said nearer information layer when said recording layer is in state (a), and $R_a[\%]$ is the reflectivity of the same when it is in state (b).

5. The optical information recording medium, as set forth in claim 3, wherein;

an information layer positioned nearer than the farthest information layer from the incidence side of said laser beam has at least a first dielectric layer, a phase-change recording layer, a second dielectric layer and a metallic reflecting layer, and said layers are arranged in the order, from the incidence side inward, of said first dielectric layer, said phase-change recording layer, said second dielectric layer and said metallic reflecting layer.

6. The optical information recording medium, as set forth in claim 5, wherein:

the wavelength of said laser beam is in the range of 390 nm to 430 nm, and said metallic reflecting layer consists of Ag or an alloy having Ag as its main constituent, having a configuration of:

$t_a \leq 12$ when $t_b \leq 18$, $t_a \leq 10$ when $18 < t_b \leq 22$, $t_a \leq 32-t_b$ when $22 < t_b \leq 30$ where $t_a$[nm] is the thickness of said phase-change recording layer, and $t_b$[nm] is that of said metallic reflecting layer.

7. The optical information recording medium, as set forth in claim 3, wherein:
an information layer positioned nearer than the farthest information layer from the incidence side of said laser beam has at least a first dielectric layer, a phase-change recording layer, a second dielectric layer, a metallic reflecting layer and a third dielectric layer, and
said layers are arranged in the order, from the incidence side inward, of said first dielectric layer, said phase-change recording layer, said second dielectric layer, said metallic reflecting layer and said third dielectric layer.

8. The optical information recording medium, as set forth in claim 7, wherein:
the wavelength of said laser beam is in the range of 390 nm to 430 nm, and
said metallic reflecting layer consists of at least Ag or an alloy having Ag as its main constituent, having a configuration of:

$t_a \leq 12$ when $t_b \leq 18$, $t_a \leq 38 - t_b$ when $16 < t_b \leq 18$ $t_a \leq 10$ when $18 < t_b 20$ $t_a \leq 30 - t_b$ when $20 < t_b \leq 24$ and $t_a \leq 28 - t_b$ when $24 < t_b \leq 26$ where $t_a$[nm] is the thickness of said phase-change recording layer, and $t_b$[nm] is that of said metallic reflecting layer.

9. The optical information recording medium, as set forth in any of claims 5 through 8, having a configuration of:

$A_c < A_a$ and $R_c > R_a$, or $A_c > A_a$ and $R_c < R_a$ where $A_c$[%] is the absorption index of said phase-change recording layer when said recording layer of an information layer positioned nearer than the farthest information layer from the incidence side of said laser beam is crystalline, and $A_a$[%] is the absorption index of the same when said recording layer is amorphous, and
$R_c$[%] is the reflectivity of said information layer when said recording layer is crystalline, and $R_a$[%] is the reflectivity of the same when it is amorphous.

10. An optical measuring method whereby a laser beam is converged on an optical information recording medium having two information layers, converged irradiation of the laser beam onto any of said information layers causing information signal to be recorded or reproduced, wherein
an information layer positioned nearer than the farthest information layer from the incidence side of said laser beam has a recording layer varying between two optically detectable states, and said laser beam reflected by any of said information layers is received by a photodetector to measure changes in transmittance, comprising:
a step of measuring with said photodetector the intensity of said laser beam coming out of said optical information recording medium when the area transmitting said laser beam in the recording layer contained in said nearer positioned information layer is in state (a) the intensity being represented by $S_a$, wherein
said laser beam has first been transmitted by said nearer positioned information layer, then been reflected by the farthest information layer, and again been transmitted by said nearer positioned information layer so that the laser beam comes out of said optical information recording medium,
a step of measuring with said photodetector the intensity of said laser beam coming out of said optical information recording medium when the area transmitting said laser beam in the recording layer contained in said nearer positioned information layer is in state (b), the intensity being represented by $S_b$, wherein
said laser beam has first been transmitted by said nearer positioned information layer, then been reflected by the farthest information layer, and again been transmitted by said nearer positioned information layer so that the laser beam comes out of said optical information recording medium, and
a step of deriving a change in the transmittance of said nearer positioned information layer on the basis of said $S_a$ and $S_b$.

11. An optical measuring method whereby a laser beam is converged on an optical information recording medium having three or more information layers, converged irradiation of the laser beam onto any of said information layers causing information signals to be recorded or reproduced, wherein
a plurality of information layers positioned nearer than the farthest information layer from the incidence side of said laser beam have a recording layer varying between two optically detectable states, and said laser beam reflected by any of said information layers is received by a photodetector to measure changes in transmittance,
case (a) is such case that a synthesized transmittance of said plurality of information layers is minimum value within the synthesized transmittances which are derived from combinations of said various states of the respective recording layers, and
case (b) is such case that a synthesized transmittance of said plurality of information layers is maximum value within the synthesized transmittances which are derived from combinations of said various states of the respective recording layers, and comprising;
a step of measuring with said photodetector the intensity of said laser beam coming out of said optical information recording medium when the combination of the states of the recording layers of said nearer plurality of the information layers is in the case (a), the intensity being represented by $S_a$, wherein said laser beam has first been transmitted by said nearer plurality of the information layers, then been reflected by a predetermined information layer located farther inside than the information layer that has transmitted the beam, and again been transmitted by said nearer plurality of the information layers so that the laser beam comes out of said optical information recording medium,
a step of measuring with said photodetector the intensity of said laser beam coming out of said optical information recording medium when the combination of the states of the recording layers of said nearer plurality of the information layers of in the case (b), the intensity being represented by $S_b$, wherein said laser beam has first been transmitted by said nearer plurality of the information layers, then been reflected by the farthest information layer, and again been transmitted by said nearer plurality of the information layers so that the laser beam comes out of said optical information recording medium, and a step of deriving a charge in the transmittance of said nearer plurality of the information layers on the basis of said $S_a$ and $S_b$.

12. An optical measuring method whereby a laser beam is converged on an optical information recording medium having two information layers, converged irradiation of the laser beam onto any of said information layers causing information signals to be recorded or reproduced, wherein an information layer positioned nearer than the farthest information layer from the incidence side of said laser beam has a recording layer varying between two optically detectable states, and said laser beam reflected by any of said information layers is received by a photodetector to measure changes in strength of the laser beam, comprising:

a step of measuring with said photodetector the intensity of said laser beam coming out of said optical information recording medium when the area transmitting said laser beam in the recording layer contained in said nearer positioned information layer is in state (a), the intensity being represented by $S_a$, wherein said laser beam has first been transmitted by said nearer positioned information layer, then been reflected by the farthest information layer, and again been transmitted by said nearer positioned information layer so that the laser beam comes out of said optical information recording medium, a step of measuring with said photodetector the intensity of said laser beam coming out of said optical information recording medium when the area transmitting said laser beam in the recording layer contained in said nearer positioned information layer is in state (b), the intensity being represented by $S_b$, wherein said laser beam has first been transmitted by said nearer positioned information layer, then bean reflected by the farthest information layer, and again been transmitted by said nearer positioned information layer so that the laser beam comes out of said optical information recording medium, and a step of deriving a change in the strength of the laser beam on the basis of said $S_a$ and $S_b$.

13. An optical measuring method whereby a laser beam is converged on an optical information recording medium having three or more information layers, converged irradiation of the laser beam onto any of said information layers causing information signals to be recorded or reproduced, wherein a plurality of information layers positioned nearer than the farthest information layer from the incidence side of said laser beam have a recording layer varying between two optically detectable states, and said laser beam reflected by any of said information layers is received by a photodetector to measure changes in the strength of the laser beam, case (a) is such case that a synthesized transmittance of said plurality of information layers is minimum value within the synthesized transmittances which are derived from combinations of said various states of the respective recording layers, and case (b) is such case that a synthesized transmittance of said plurality of information layers is maximum value within the synthesized transmittances which are derived from combinations of said various states of the respective recording layers, and comprising:

a step of measuring with said photodetector the intensity of said laser beam coming out of said optical information recording medium when the combination of the states of the recording layers of said nearer plurality of the information layers is in the case (a), the intensity being represented by $S_a$, wherein said laser beam has first been transmitted by said nearer plurality of the information layers, then been reflected by a predetermined information layer located farther inside than the information layer that has transmitted the beam, and again been transmitted by said nearer plurality of the information layers so that the laser beam comes out of said optical information recording medium, a step of measuring with said photodetector the intensity of said laser beam coming out of said optical information recording medium when the combination of the states of the recording layers off said nearer plurality off the information layers is in the case (b), the intensity being represented by $S_b$, wherein said laser beam has first been transmitted by said nearer plurality of the information layers, then been reflected by the farthest information layer, and again been transmitted by said nearer plurality of the information layers so that the laser beam comes out of said optical information recording medium, and step of deriving a change in the strength of the laser beam on the basis of said $S_a$ and $S_b$.

14. An optical measuring method whereby a laser beam is converged on an optical information recording medium having two information layers, converged irradiation of the laser beam onto any of said information layers causing information signals to be recorded or reproduced, wherein an information layer positioned nearer than the farthest information layer from the incidence side of said laser beam has a recording layer varying between two optically detectable states, and said laser beam reflected by any of said information layers is received by a photodetector to measure changes in transmittance, comprising:

a step of measuring with said photodetector a modulation amplitude of said laser beam coming out of said optical information recording medium when the area transmitting said laser beam in the recording layer contained in said nearer positioned information layer is in state (a), the modulation amplitude being represented by $A_1$, wherein the laser beam has first been transmitted by said nearer positioned information layer, then been modulated by said information signals recorded on the farthest information layer, and again been transmitted by said nearer positioned information layer so that the laser beam comes out of said optical information recording medium, a step of measuring with said photodetector the modulation amplitude of said laser beam coming out of said optical information recording medium when a part of or the whole of the area transmitting said laser beam in the recording layer contained in said nearer positioned information layer is in state (b), the modulation amplitude being represented by $A_2$, wherein the layer beam has first been transmitted by said nearer positioned information layer, then been modulated by said information signals recorded on the farthest information layer, and again been transmitted by said nearer positioned information layer so that the laser beam comes out of said optical information recording medium, and a step of deriving a change in the transmittance of said nearer positioned information layer on the basis of said $A_1$ and $A_2$.

15. An optical measuring method whereby a laser beam is converged on an optical information recording medium having three or more information layers, converged irradiation of the laser beam onto any of said information layers causing information signals to be recorded or reproduced, wherein a plurality of the information layers positioned nearer than the farthest information layer from the incidence side off said laser beam have a recording layers each varying between two optically detectable states, and said laser beam reflected by any of said information layers is received by a photodetector to measure changes in transmittance, and case (a) is such case that a synthesized transmittance of said plurality of information layers is minimum value within the synthesized transmittances which are derived from combinations of said various states of the respective recording layers, and case (b) is such case that a synthesized transmittance of said plurality of information layers is maximum value within the synthesized transmittances which are derived from combinations of said various states of the respective recording layers, and comprising;

a step of measuring with said photodetector a modulation amplitude of said laser beam coming out of said optical information recording medium when the combination of the states of the recording layers of said nearer plurality of the information layers is in the case (a), the modulation amplitude being represented by $A_1$, wherein the laser beam has first been transmitted by said nearer plurality of the information layers, then been modulated by said information signals recorded on a predetermined information layer located farther inside than the information layer that has transmitted the beam, and again been transmitted by said nearer plurality or the information layers so that the laser beam comes out of said optical information recording medium, a step of measuring with said photodetector a modulation amplitude of said laser beam coming out of said optical information recording medium when the combination of the states of the recording layers of said nearer plurality of the information layers is in the case (b), the modulation amplitude being represented by $A_2$, wherein the laser beam has first been transmitted by said nearer plurality of the information layers, then been modulated by said information signals recorded on the farthest information layer, and again been transmitted by said nearer plurality of the information layers so that the laser beam comes out of said optical information recording medium, and a step of deriving a change in the transmittance of said nearer positioned information layer on the basis of said $A_1$ and $A_2$.

16. An optical measuring method whereby a laser beam is converged on an optical information recording medium having two information layers, converged irradiation of the laser beam onto any of said information layers causing information signals to be recorded or reproduced, wherein an information layer positioned nearer than the farthest information layer from the incidence side of said laser beam has a recording layer varying between two optically detectable states, and said laser beam reflected by any of said information layers is received by a photodetector to measure changes in a modulation amplitude of the laser beam, comprising:

a step of measuring with said photodetector a modulation amplitude of said laser beam coming out of said optical information recording medium when the area transmitting said laser beam in the recording layer contained in said nearer positioned information layer is in state (a), the modulation amplitude being represented by $A_1$, wherein the laser beam has first been transmitted by said nearer positioned information layer, then been modulated by said information signal recorded on the farthest information layer, and again been transmitted by said nearer positioned information layer so that the laser beam comes out of said optical information recording the medium, a step of measuring with said photodetector the modulation amplitude of said laser beam coming out of said optical information recording medium when a part of or the whole of the area transmitting said laser beam in the recording layer contained in said nearer positioned information layer is in state (b), the modulation amplitude being represented by $A_2$, wherein the laser beam has first been transmitted by said nearer positioned information layer, then been modulated by said information signals recorded on the farthest information layer, and again been transmitted by said nearer positioned information layer so that the laser beam comes out of said optical information recording medium, and a step of deriving a change in the modulation amplitude of the laser beam on the basis of said $A_1$ and $A_2$.

17. An optical measuring method whereby a laser beam is converged on an optical information recording medium having three or more information layers, converged irradiation of the laser beam onto any of said information layers causing information signals to be recorded or reproduced, wherein a plurality of the information layers positioned nearer than the farthest information layer from the incidence side of said laser beam have a recording layers each varying between two optically detectable states, and said laser beam reflected by any of said information layers is received by a photodetector to measure changes in a modulation amplitude of the laser beam, and case (a) is such case that a synthesized transmittance of said plurality of information layers is minimum value within the synthesized transmittances which are derived from combinations of said various states of the respective recording layers, and case (b) is such case that a synthesized transmittance of said plurality of information layers is maximum value within the synthesized transmittances which are derived from combinations of said various states of the respective recording layers, and comprising:

a step of measuring with said photodetector a modulation amplitude of said laser beam coming out of said optical information recording medium when the combination of the states of the recording layers of said nearer plurality of the information layers is in the case (a), the modulation amplitude being represented by $A_1$, wherein the laser beam has first been transmitted by said nearer plurality of the information layers, then been modulated by said information signals recorded on a predetermined information layer located farther inside than the information layer that has transmitted the beam, and again been transmitted by said nearer plurality of the information layers so that the laser beam comes out of said optical information recording medium, a step of measuring with said photodetector a modulation amplitude of said laser beam coming out of said optical information recording medium when the combination of the states of the recording layers of said nearer plurality of the information layers is in the case (b), the modulation amplitude being represented by $A_2$, wherein the laser beam has first been transmitted by said nearer plurality of the information layers, then been modulated by said information signals recorded on the farthest information layer, and again been transmitted by said nearer plurality of the information layers so that the laser beam comes out of said optical information recording medium, and a step of deriving a change in the modulation amplitude of the laser beam on the basis of said $A_1$ and $A_2$.

18. An optical measuring method as set forth in claim 16 or 17, wherein the difference $A_1$, between a zero level and upper envelope of the modulation amplitude is measured instead of the modulation amplitude A1 of the laser beam, the difference $A_2$, between a zero level and upper envelope of the modulation amplitude is measured instead of the modulation amplitude $A_2$ of the laser beam, and the change in the upper envelope of the modulation amplitude of the laser beam is detected on the basis of the $A_1$ and $A_2$ instead of that the change in the modulation amplitude of the laser beam is detected on the basis of the $A_1$ and $A_2$.

19. The optical measuring method, as set forth in claim 14, whereby, when the area in which said laser beam transmits of the recording layer contained in the nearer information layer is in state (b), after recording information signals on the farthest information layer, the modulation amplitude $A_2$ is measured.

20. The optical measuring method, as set forth in claim 10, 12, 14, 16 or 19, wherein said state (a) is a crystalline state and said state (b) is an amorphous state.

21. The optical measuring method, as set forth in claim 20, wherein the recording layer of said nearer positioned information layer is, when said $S_b$ or $A_2$, or $A_{2'}$ is be measured, in a state consisting of many recording marks in an amorphous state and crystalline portions around them.

22. The optical measuring method, as set forth in claim 10, 12, 13, 16, or 19, said state (a) is an amorphous state and said state (b) is a crystalline state.

23. The optical measuring method, as set forth in claim 22, wherein the recording layer of said nearer positioned information layer is, when said $S_b$ or $A_2$ or $A_{2'}$ is be measured, in a state consisting of many recording marks in a crystalline state and amorphous portions around them.

24. An optical information recording medium having a configuration of:

$$0 \leq |1+(S_b/S_a)^{1/2}| \leq 0.1\alpha$$

where $\alpha$ is the ratio of the area of said recording mark portion to the area where said laser beam is transmitted when said $S_b$ used in the optical measuring method described in claim 10 is measured.

25. An optical information recording medium having a configuration of:

$$0 \leq |1-(A_2/A_1)^{1/2}| \leq 0.1\alpha$$

where $\alpha$ is the ratio of the area of said recording mark portion to the area where said laser beam is transmitted when said $A_2$ used in the optical measuring method described in claim 14 is measured.

26. An optical information recording/reproducing method of recording or reproducing information signals by irradiating the optical information recording medium stated in claim 1, 3, 5, 6, 7, 8, 24 or 25, with a laser beam, whereby:

information signals are recorded or reproduced by irradiating one of two or more information layers with said laser beam from one side of said optical information recording medium.

* * * * *

UNITED STATES PATENT AND TRADEMARK OFFICE
CERTIFICATE OF CORRECTION

PATENT NO. : 6,893,698 B2
DATED : May 17, 2005
INVENTOR(S) : Narumi et al.

It is certified that error appears in the above-identified patent and that said Letters Patent is hereby corrected as shown below:

Column 29,
Line 25, delete "$t_a \leq 10$ when $18 < t_b 20$" and insert -- $t_a \leq 10$ when $18 < t_b \leq 20$ --.

Column 30,
Line 60, delete "of" and insert -- is --.

Column 31,
Line 1, delete "charge" and insert -- change --.

Column 32,
Line 15, delete the first and second occurrences of "off" and replace both with -- of --.
Line 56, delete "layer" and insert -- laser --.

Column 33,
Line 6, delete "off" and insert -- of --.
Line 33, delete "or" and insert -- of --.

Column 34,
Line 5, delete "signal" and insert -- signals --.

Signed and Sealed this

Eighth Day of November, 2005

JON W. DUDAS
*Director of the United States Patent and Trademark Office*